United States Patent
Songer et al.

(10) Patent No.: US 8,262,731 B2
(45) Date of Patent: Sep. 11, 2012

(54) ARTIFICIAL DISC DEVICE

(75) Inventors: Matthew N. Songer, Marquette Township, MI (US); Thomas S. Kilpela, Marquette, MI (US); Brian P. Janowski, Marquette, MI (US); Gregory A. Berrevoets, Skandia, MI (US); Matthew P. Gephart, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 184 days.

(21) Appl. No.: 11/184,625

(22) Filed: Jul. 19, 2005

(65) Prior Publication Data

US 2005/0256581 A1    Nov. 17, 2005

Related U.S. Application Data

(63) Continuation of application No. 10/282,620, filed on Oct. 29, 2002, now Pat. No. 7,001,433.

(60) Provisional application No. 60/382,758, filed on May 23, 2002.

(51) Int. Cl.
*A61F 2/44* (2006.01)

(52) U.S. Cl. ............... 623/17.14; 623/17.11; 623/17.15; 623/17.16

(58) Field of Classification Search ............ 606/61; 623/17.11–17.16
See application file for complete search history.

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 3,975,778 A | 8/1976 | Newton, III |
| 4,021,382 A | 5/1977 | Stoy et al. |
| 4,081,402 A | 3/1978 | Levy et al. |
| 4,147,764 A | 4/1979 | Levy et al. |
| 4,309,777 A | 1/1982 | Patil |
| 4,349,921 A | 9/1982 | Kuntz |

(Continued)

FOREIGN PATENT DOCUMENTS

CA    2395609 A1    2/2001

(Continued)

OTHER PUBLICATIONS

Bao, Qi-Bin and Yuan, Hansen A., "Artificial Disc Technology", *Neurosurg. Focus*, vol. 9, No. 4, Oct. 2000, 7 pp.

(Continued)

*Primary Examiner* — Eduardo C Robert
*Assistant Examiner* — Julianna N Harvey
(74) *Attorney, Agent, or Firm* — Fitch, Even, Tabin & Flannery, LLP

(57) ABSTRACT

Artificial disc devices are disclosed that restore correct anatomical intervertebral spacing for damaged discs while maintaining a substantially normal range of biomechanical movement for the vertebrae between which they are implanted. The disc devices include center bearing and outer or annular bearing portions with the center bearing portion including generally axially extending locating surfaces which cooperate with the facing vertebral surfaces to resist migration. The outer bearing portion is for load bearing or load sharing with the center bearing portion and includes surfaces that extend radially toward the periphery of the vertebrae so that subsidence about the center bearing portion is minimized. Alternate forms of the disc devices include one with an axially enlarged center ball bearing having an annular ring bearing extending thereabout and another having upper and lower plate members with a central bumper member and a surrounding resilient annular member therebetween.

8 Claims, 22 Drawing Sheets

U.S. PATENT DOCUMENTS

| | | | |
|---|---|---|---|
| 4,650,490 A | 3/1987 | Figgie, III | |
| 4,714,469 A | 12/1987 | Kenna | |
| 4,759,766 A * | 7/1988 | Buettner-Janz et al. | 623/17.15 |
| 4,759,769 A * | 7/1988 | Hedman et al. | 623/17.13 |
| 4,863,476 A | 9/1989 | Shepperd | |
| 4,863,477 A | 9/1989 | Monson | |
| 4,917,704 A | 4/1990 | Frey et al. | |
| 4,932,969 A | 6/1990 | Frey et al. | |
| 4,936,848 A | 6/1990 | Bagby | |
| 4,946,378 A | 8/1990 | Hirayama et al. | |
| 4,997,432 A * | 3/1991 | Keller | 606/61 |
| 5,002,576 A | 3/1991 | Fuhrmann et al. | |
| 5,035,716 A | 7/1991 | Downey | |
| 5,047,055 A | 9/1991 | Bao et al. | |
| 5,071,437 A | 12/1991 | Steffee | |
| 5,108,438 A | 4/1992 | Stone | |
| 5,127,920 A | 7/1992 | MacArthur | |
| 5,133,759 A | 7/1992 | Turner | |
| 5,133,772 A | 7/1992 | Hack et al. | |
| 5,147,404 A | 9/1992 | Downey | |
| 5,171,281 A | 12/1992 | Parsons et al. | |
| 5,176,710 A | 1/1993 | Hahn et al. | |
| 5,192,326 A | 3/1993 | Bao et al. | |
| 5,258,031 A | 11/1993 | Salib et al. | |
| 5,258,043 A | 11/1993 | Stone | |
| 5,273,742 A | 12/1993 | Gould et al. | |
| 5,306,308 A | 4/1994 | Gross et al. | |
| 5,306,309 A | 4/1994 | Wagner et al. | |
| 5,314,477 A | 5/1994 | Marnay | |
| 5,320,625 A | 6/1994 | Bertin | |
| 5,320,644 A | 6/1994 | Baumgartner | |
| 5,401,269 A * | 3/1995 | Buttner-Janz et al. | 623/17.15 |
| 5,425,773 A * | 6/1995 | Boyd et al. | 623/17.15 |
| 5,458,642 A | 10/1995 | Beer et al. | |
| 5,458,643 A | 10/1995 | Oka et al. | |
| 5,507,816 A | 4/1996 | Bullivant | |
| 5,514,180 A | 5/1996 | Heggeness et al. | |
| 5,522,899 A | 6/1996 | Michelson | |
| 5,534,028 A | 7/1996 | Bao et al. | |
| 5,549,679 A | 8/1996 | Kuslich | |
| 5,556,431 A | 9/1996 | Büttner-Janz | |
| 5,556,433 A | 9/1996 | Gabriel et al. | |
| 5,562,736 A | 10/1996 | Ray et al. | |
| 5,562,738 A | 10/1996 | Boyd et al. | |
| 5,571,189 A * | 11/1996 | Kuslich | 623/17.12 |
| 5,595,563 A | 1/1997 | Moisdon | |
| 5,609,643 A | 3/1997 | Colleran et al. | |
| 5,645,596 A | 7/1997 | Kim et al. | |
| 5,645,597 A | 7/1997 | Krapiva | |
| 5,658,336 A | 8/1997 | Pisharodi | |
| 5,665,122 A | 9/1997 | Kambin | |
| 5,674,295 A | 10/1997 | Ray et al. | |
| 5,674,296 A * | 10/1997 | Bryan et al. | 623/17.16 |
| 5,676,701 A | 10/1997 | Yuan et al. | |
| 5,676,702 A | 10/1997 | Ratron | |
| 5,683,465 A | 11/1997 | Shinn et al. | |
| 5,693,100 A | 12/1997 | Pisharodi | |
| 5,702,450 A | 12/1997 | Bisserie | |
| 5,716,416 A | 2/1998 | Lin | |
| 5,728,762 A | 3/1998 | Reich et al. | |
| 5,755,797 A | 5/1998 | Baumgartner | |
| 5,755,798 A | 5/1998 | Papavero et al. | |
| 5,782,832 A | 7/1998 | Larsen et al. | |
| 5,824,093 A | 10/1998 | Ray et al. | |
| 5,824,094 A | 10/1998 | Serhan et al. | |
| 5,860,980 A | 1/1999 | Axelson, Jr. et al. | |
| 5,865,845 A | 2/1999 | Thalgott | |
| 5,865,846 A | 2/1999 | Bryan et al. | |
| 5,888,223 A | 3/1999 | Bray, Jr. | |
| 5,888,226 A * | 3/1999 | Rogozinski | 623/17.16 |
| 5,893,889 A * | 4/1999 | Harrington | 623/17.16 |
| 5,895,428 A | 4/1999 | Berry | |
| 5,899,941 A | 5/1999 | Nishijima et al. | |
| 5,919,235 A | 7/1999 | Husson et al. | |
| 5,964,807 A | 10/1999 | Gan et al. | |
| 5,976,186 A | 11/1999 | Bao et al. | |
| 5,980,572 A | 11/1999 | Kim et al. | |
| 6,001,130 A | 12/1999 | Bryan et al. | |
| 6,019,793 A | 2/2000 | Perren et al. | |
| 6,022,376 A | 2/2000 | Assell et al. | |
| 6,039,763 A | 3/2000 | Shelokov | |
| RE36,758 E | 6/2000 | Fitz | |
| 6,074,390 A | 6/2000 | Zucherman et al. | |
| 6,093,205 A | 7/2000 | McLeod et al. | |
| 6,093,207 A | 7/2000 | Pisharodi | |
| 6,110,210 A | 8/2000 | Norton et al. | |
| 6,113,639 A | 9/2000 | Ray et al. | |
| 6,127,597 A | 10/2000 | Beyar et al. | |
| 6,132,465 A | 10/2000 | Ray et al. | |
| 6,136,031 A | 10/2000 | Middleton | |
| 6,139,579 A | 10/2000 | Steffee et al. | |
| 6,143,031 A | 11/2000 | Knothe et al. | |
| 6,146,422 A | 11/2000 | Lawson | |
| 6,156,067 A | 12/2000 | Bryan et al. | |
| 6,162,252 A | 12/2000 | Kuras et al. | |
| 6,179,874 B1 * | 1/2001 | Cauthen | 623/17.14 |
| 6,183,518 B1 | 2/2001 | Ross et al. | |
| 6,187,048 B1 | 2/2001 | Milner et al. | |
| 6,190,387 B1 | 2/2001 | Zucherman et al. | |
| 6,206,924 B1 | 3/2001 | Timm | |
| 6,224,630 B1 | 5/2001 | Bao et al. | |
| 6,240,926 B1 | 6/2001 | Chin Gan et al. | |
| 6,251,140 B1 | 6/2001 | Marino et al. | |
| 6,264,695 B1 | 7/2001 | Stoy | |
| 6,280,475 B1 | 8/2001 | Bao et al. | |
| 6,283,968 B1 | 9/2001 | Mehdizadeh | |
| 6,283,998 B1 | 9/2001 | Eaton | |
| 6,315,795 B1 | 11/2001 | Scarborough et al. | |
| 6,315,797 B1 | 11/2001 | Middleton | |
| 6,348,071 B1 | 2/2002 | Steffee et al. | |
| 6,352,557 B1 | 3/2002 | Ferree | |
| 6,368,350 B1 | 4/2002 | Erickson et al. | |
| 6,371,990 B1 | 4/2002 | Ferree | |
| 6,375,682 B1 | 4/2002 | Fleischmann et al. | |
| 6,395,032 B1 | 5/2002 | Gauchet | |
| 6,402,784 B1 | 6/2002 | Wardlaw | |
| 6,402,785 B1 | 6/2002 | Zdeblick et al. | |
| 6,419,704 B1 | 7/2002 | Ferree | |
| 6,428,544 B1 | 8/2002 | Ralph et al. | |
| 6,428,575 B2 | 8/2002 | Koo et al. | |
| 6,432,106 B1 | 8/2002 | Fraser | |
| 6,432,107 B1 | 8/2002 | Ferree | |
| 6,432,140 B1 | 8/2002 | Lin | |
| 6,436,098 B1 | 8/2002 | Michelson | |
| 6,436,101 B1 | 8/2002 | Hamada | |
| 6,436,102 B1 | 8/2002 | Ralph et al. | |
| 6,436,140 B1 | 8/2002 | Liu et al. | |
| 6,436,141 B2 | 8/2002 | Castro et al. | |
| 6,436,142 B1 | 8/2002 | Paes et al. | |
| 6,436,146 B1 | 8/2002 | Hassler et al. | |
| 6,440,168 B1 | 8/2002 | Cauthen | |
| 6,440,170 B1 | 8/2002 | Jackson | |
| 6,478,822 B1 * | 11/2002 | Leroux et al. | 623/17.14 |
| 6,488,716 B1 | 12/2002 | Huang et al. | |
| 6,508,839 B1 | 1/2003 | Lambrecht et al. | |
| 6,517,580 B1 * | 2/2003 | Ramadan et al. | 623/17.15 |
| 6,527,804 B1 | 3/2003 | Gauchet et al. | |
| 6,540,785 B1 | 4/2003 | Gill et al. | |
| 6,547,823 B2 | 4/2003 | Scarborough et al. | |
| 6,562,047 B2 | 5/2003 | Ralph et al. | |
| 6,579,320 B1 | 6/2003 | Gauchet et al. | |
| 6,579,321 B1 * | 6/2003 | Gordon et al. | 623/17.16 |
| 6,582,466 B1 | 6/2003 | Gauchet | |
| 6,592,624 B1 | 7/2003 | Fraser et al. | |
| 6,602,291 B1 | 8/2003 | Ray et al. | |
| 6,610,091 B1 | 8/2003 | Reiley | |
| 6,679,915 B1 | 1/2004 | Cauthen | |
| 6,682,562 B2 * | 1/2004 | Viart et al. | 623/17.14 |
| 6,743,257 B2 | 6/2004 | Castro | |
| 6,770,095 B2 | 8/2004 | Grinberg et al. | |
| 6,783,550 B2 | 8/2004 | MacArthur | |
| 6,793,678 B2 * | 9/2004 | Hawkins | 623/17.15 |
| 6,899,716 B2 | 5/2005 | Cragg | |
| 6,936,071 B1 | 8/2005 | Marnay et al. | |
| 7,001,433 B2 | 2/2006 | Songer et al. | |
| 7,156,876 B2 | 1/2007 | Moumene et al. | |
| 2001/0010021 A1 | 7/2001 | Boyd et al. | |

| | | |
|---|---|---|
| 2001/0012938 A1 | 8/2001 | Zucherman et al. |
| 2001/0016772 A1 | 8/2001 | Lee et al. |
| 2001/0016773 A1 | 8/2001 | Serhan et al. |
| 2001/0016776 A1 | 8/2001 | Zuckerman et al. |
| 2001/0020476 A1 | 9/2001 | Gan et al. |
| 2001/0027343 A1 | 10/2001 | Keller |
| 2001/0032019 A1 | 10/2001 | Van Dyke et al. |
| 2001/0032020 A1 | 10/2001 | Besselink |
| 2001/0047208 A1 | 11/2001 | Michelson |
| 2001/0051829 A1 | 12/2001 | Middleton |
| 2002/0013600 A1 | 1/2002 | Scribner et al. |
| 2002/0022883 A1 | 2/2002 | Burg |
| 2002/0022888 A1 | 2/2002 | Serhan et al. |
| 2002/0026244 A1 | 2/2002 | Trieu |
| 2002/0029082 A1 | 3/2002 | Muhanna |
| 2002/0029083 A1 | 3/2002 | Zucherman et al. |
| 2002/0035400 A1 * | 3/2002 | Bryan et al. ............... 623/17.15 |
| 2002/0045942 A1 | 4/2002 | Ham |
| 2002/0045944 A1 | 4/2002 | Muhanna et al. |
| 2002/0049498 A1 | 4/2002 | Yuksel et al. |
| 2002/0082608 A1 | 6/2002 | Reiley et al. |
| 2002/0082701 A1 | 6/2002 | Zdeblick et al. |
| 2002/0087480 A1 | 7/2002 | Sauriol et al. |
| 2002/0099444 A1 | 7/2002 | Boyd et al. |
| 2002/0106393 A1 | 8/2002 | Bianchi et al. |
| 2002/0107571 A1 | 8/2002 | Foley |
| 2002/0107572 A1 | 8/2002 | Foley |
| 2002/0107573 A1 | 8/2002 | Steinberg |
| 2002/0120269 A1 | 8/2002 | Lange |
| 2002/0120270 A1 | 8/2002 | Trieu et al. |
| 2002/0120334 A1 | 8/2002 | Crozet |
| 2002/0120336 A1 | 8/2002 | Santilli |
| 2002/0156528 A1 | 10/2002 | Gau |
| 2002/0165612 A1 | 11/2002 | Gerber et al. |
| 2003/0009226 A1 | 1/2003 | Graf |
| 2003/0023311 A1 | 1/2003 | Trieu |
| 2003/0028197 A1 | 2/2003 | Hanson et al. |
| 2003/0028251 A1 | 2/2003 | Mathews |
| 2003/0040799 A1 | 2/2003 | Boyd et al. |
| 2003/0045939 A1 | 3/2003 | Casutt |
| 2003/0055427 A1 | 3/2003 | Graf |
| 2003/0074076 A1 | 4/2003 | Ferree et al. |
| 2003/0100951 A1 | 5/2003 | Serhan et al. |
| 2003/0135276 A1 | 7/2003 | Eckman |
| 2003/0135277 A1 | 7/2003 | Bryan et al. |
| 2003/0135278 A1 | 7/2003 | Eckman |
| 2003/0176921 A1 | 9/2003 | Lawson |
| 2003/0204260 A1 | 10/2003 | Ferree |
| 2003/0204261 A1 * | 10/2003 | Eisermann et al. ........ 623/17.14 |
| 2003/0220691 A1 | 11/2003 | Songer et al. |
| 2003/0233146 A1 * | 12/2003 | Grinberg et al. ........... 623/17.14 |
| 2004/0024462 A1 | 2/2004 | Ferree et al. |
| 2004/0030391 A1 | 2/2004 | Ferree |
| 2004/0044410 A1 | 3/2004 | Ferree et al. |
| 2004/0082999 A1 | 4/2004 | Mathys, Jr. et al. |
| 2004/0093082 A1 | 5/2004 | Ferree |
| 2004/0102846 A1 | 5/2004 | Keller et al. |
| 2004/0117019 A1 | 6/2004 | Trieu et al. |
| 2004/0117022 A1 | 6/2004 | Marnay et al. |
| 2004/0133278 A1 | 7/2004 | Marino et al. |
| 2004/0153157 A1 | 8/2004 | Keller |
| 2005/0021042 A1 | 1/2005 | Marnay et al. |
| 2005/0021143 A1 | 1/2005 | Keller |
| 2005/0033437 A1 | 2/2005 | Bao et al. |
| 2005/0071011 A1 | 3/2005 | Ralph et al. |
| 2005/0085911 A1 | 4/2005 | Link |
| 2005/0085917 A1 | 4/2005 | Marnay et al. |
| 2005/0165485 A1 | 7/2005 | Trieu |
| 2005/0192671 A1 | 9/2005 | Bao et al. |
| 2005/0266581 A1 | 12/2005 | Droit et al. |
| 2006/0004453 A1 | 1/2006 | Bartish, Jr. et al. |
| 2006/0020342 A1 | 1/2006 | Ferree et al. |
| 2006/0041614 A1 | 2/2006 | Oe |
| 2006/0212122 A1 | 9/2006 | Perera |
| 2006/0235527 A1 | 10/2006 | Buettner-Janz et al. |
| 2006/0235528 A1 | 10/2006 | Buettner-Janz |
| 2006/0235531 A1 | 10/2006 | Buettner-Janz |
| 2007/0027547 A1 | 2/2007 | Rydell et al. |
| 2007/0100454 A1 | 5/2007 | Burgess et al. |

FOREIGN PATENT DOCUMENTS

| | | |
|---|---|---|
| CA | 2482403 | 10/2002 |
| CA | 2548780 | 12/2004 |
| CN | 1697633 | 11/2000 |
| DE | 9000094 | 1/1999 |
| DE | 29911422 | 8/1999 |
| DE | 10130825 | 3/2002 |
| DE | 202005005405 | 6/2005 |
| EP | 0 179 695 A1 | 4/1986 |
| EP | 0 346 129 A1 | 12/1989 |
| EP | 0 773 008 A1 | 5/1997 |
| EP | 0 919 209 A1 | 6/1999 |
| EP | 1 104 665 A1 | 6/2001 |
| EP | 1 205 160 | 5/2002 |
| FR | 2 372 622 | 6/1978 |
| FR | 2 723 841 A1 | 3/1996 |
| FR | 2 787 014 | 6/2000 |
| FR | 2 797 179 | 2/2001 |
| FR | 2 799 116 A1 | 4/2001 |
| FR | 2 805 985 | 9/2001 |
| FR | 2824261 | 11/2002 |
| JP | 63300758 A2 | 12/1988 |
| JP | 1308557 A2 | 12/1989 |
| JP | 01142293 A | 4/1990 |
| JP | 02111358 A | 4/1990 |
| JP | 2215461 A2 | 8/1990 |
| JP | 2224659 A2 | 9/1990 |
| JP | 2224660 A2 | 9/1990 |
| JP | 03275055 A | 12/1991 |
| JP | 03275056 A | 12/1991 |
| JP | 04303444 A | 10/1992 |
| JP | 05277141 A | 10/1993 |
| JP | 06-285099 A | 10/1994 |
| JP | 08098850 A | 4/1996 |
| JP | 08098851 A2 | 4/1996 |
| JP | 11009618 A | 1/1999 |
| JP | 11137585 A | 5/1999 |
| WO | WO 90/11740 A1 | 10/1990 |
| WO | 9105521 | 5/1991 |
| WO | WO 91/16867 A1 | 11/1991 |
| WO | WO 93/16664 A1 | 9/1993 |
| WO | WO 95/00082 A1 | 1/1995 |
| WO | WO 96/01598 A1 | 1/1996 |
| WO | WO 96/11642 A1 | 4/1996 |
| WO | WO 96/27339 A1 | 9/1996 |
| WO | WO 98/05274 A1 | 2/1998 |
| WO | WO9819617 | 5/1998 |
| WO | WO 98/55053 A1 | 12/1998 |
| WO | WO 99/11203 A1 | 3/1999 |
| WO | WO 99/22675 A1 | 5/1999 |
| WO | WO 99/30651 A1 | 6/1999 |
| WO | WO 00/13619 A1 * | 3/2000 |
| WO | WO0042953 | 7/2000 |
| WO | WO 01/15638 A1 | 3/2001 |
| WO | WO 01/32100 A2 | 5/2001 |
| WO | WO 01/68003 A1 | 9/2001 |
| WO | 02/087480 | 11/2002 |
| WO | WO03035129 | 5/2003 |
| WO | WO03099172 | 12/2003 |
| WO | WO2005009298 | 2/2005 |
| WO | WO2005041818 | 5/2005 |
| WO | WO2005051240 | 6/2005 |
| WO | 2006016384 | 2/2006 |
| WO | 2006061114 | 6/2006 |

OTHER PUBLICATIONS

Feder, Barnaby J., "When F.D.A. Says Yes, but Insurers Say No", *The New York Times*, Jul. 6, 2005, 2 pp.

Charité Artificial Disc Product Catalog, DePuy Spine, Inc., Dec. 2004, 16 pp.

Charité Artificial Disc Centerline™ TDR Instrumentation, DePuy Spine, Inc., Dec. 2004, 20 pp.

Zdeblick, Thomas A. et al., "Cervical Interbody Fusion Cages", Spine, vol. 23, No. 7, 1998, pp. 758-765.

European Search Report dated Feb. 20, 2008 corresponding to European Patent Application No. 03738960.8-2310.

Bao, Q. et al, Artificial Disc Technology, Nerosurg. Focus, vol. 9, Oct. 2000, 7 pp.

The State Intellectual Property Office of China, First Notification of Office Action issued corresponding to Application No. 200780040650.7, Dec. 15, 2010, 9 pp.

European Patent Office, Supplementary Search Report issued corresponding to Application No. EP 07 84 2616, Mar. 20, 2012, 7 pp.

European Patent Office, Supplementary Partial Search Report issued corresponding to Application No. EP04796064, Mar. 22, 2012, 8 pp.

* cited by examiner

ARTIFICIAL DISC DEVICE

CROSS-REFERENCE TO RELATED APPLICATION

This application is a continuation of U.S. patent application Ser. No. 10/282,620, filed Oct. 29, 2002 now U.S. Pat. No. 7,001,433, entitled "Artificial Disc Device," which claims priority to U.S. Provisional Application No. 60/382,758, filed May 23, 2002, entitled "Artificial Intervertebral Disc Device," and which are incorporated by reference herein in its entirety.

BACKGROUND OF THE INVENTION

Artificial disc technology has been employed to correct damaged spinal discs for relieving back pain and restoring or maintaining intervertebral spacing while attempting to minimize their constraining effects on the normal biomechanical movement of the spine. Two types of artificial discs have generally been employed: the artificial total disc which is designed to substitute for the entire disc, i.e. the annulus, nucleus and possibly the end plates as well; and the artificial nucleus where only the nucleus is replaced with the annulus and end plates remaining intact. The disc of the present invention is not intended to be limited to one or the other of the above types.

A number of prior artificial disc devices include upper and lower members that are rigidly fixed to the adjacent upper and lower vertebrae. These fixed members sandwich a bearing therebetween along which they can slide to allow for relative movement between the adjacent vertebrae, see, e.g. U.S. Patent Application Publication 2002/0035400. However, devices such as these usually require special surface materials and/or surface treatments that allow for bone ingrowth for fixing the members to the vertebrae. Moreover, these devices have had problems with migration where the intermediate bearing body shifts out from between the vertebrae, and thus generally require more complex shapes to form stops for resisting such disc shifting.

In a relatively early approach, a stainless steel ball was employed in the damaged disc area. The ball approach, while effective to provide a good range of motion, tended to create subsidence problems. Over time, the ball would crush into the end plates as loading was fairly concentrated over a small surface on the ball in engagement with the plates. In other words, since these ball implants were not of a size that enabled the load of the spine to be distributed evenly thereacross, the end plates tended to subside or fall around the ball.

There also has been focus on simply replacing the nucleus with a gelled substance either injected directly in the disc or provided in pouches to attempt to reinflate the annulus and provide for load bearing. However, these approaches are limited in their use to patients who have a substantially undamaged disc annulus.

Accordingly, there is a need for an artificial disc that does not significantly inhibit spine movement while still providing the load bearing and spacer functions akin to that of a normal, healthy spinal disc.

SUMMARY OF THE INVENTION

In accordance with one form of the present invention, an artificial disc device is provided including a central, enlarged bearing portion and an outer, annular bearing portion generally extending about the central bearing portion and allowing for movement therebetween. The inner or central, enlarged bearing portion preferably has a body including upper and lower arcuate surfaces or surface portions that can shift relative to the outer bearing portion as well as with respect to the confronting surfaces of the spine, such as the end plates of the vertebrae. In this regard, the arcuate surfaces are not rigidly fixed to the vertebrae and are curved so as to allow the upper and lower vertebrae to shift with respect to each other such as when the spine is bent from side to side or front to back and twists or turns. At the same time, the enlarged central bearing portion can engage in small indentations in the respective vertebral surfaces that keeps the central bearing in a relative locked position thereby preventing lateral shifting with respect to the vertebrae so that the implant does not migrate despite the shifting vertebrae above and below these bearing surfaces. Thus, the enlarged central bearing portion locates the artificial disc device relative to the vertebrae.

The main body of the central bearing or bearing portion or bearing assembly including the arcuate bearing surfaces thereof can be a hard metallic material or alloy for load bearing purposes. Alternatively, a hard plastic could be employed to provide the central bearing portion with resiliency under compressive loading. For shock absorption, the bearing body may be provided with a hollow core or one that is liquid or gel filled or filled with other elastic material. To vary the give or compressibility of the central bearing body, the size of the core could be enlarged or decreased accordingly, or the modulus of elasticity of the body material can be varied.

In one preferred form, the outer bearing portion has a body that includes radially inner surfaces adjacent the arcuate surfaces adapted or configured for allowing relative movement therebetween. The outer bearing shares the compressive loading generated between the vertebrae via upper and lower bearing surfaces or surface portions thereof so that the load is better distributed across the present artificial disc device minimizing localized forces thereon. With the provision of the outer bearing, the present device is well suited to avoid subsidence problems as could occur in prior devices having highly localized loading thereon.

The outer bearing or bearing assembly also may be constructed to provide improved shock absorption capabilities such as with an inner portion of the body that is softer than the harder outer portion. For example, an elastomeric layer of material can be employed between attached upper and lower bearing plates of the outer bearing, or the core layer of an annular portion and/or an inner ball bearing portion of the outer bearing can be of elastomeric or liquid gelled material. Manifestly, material combinations can also be employed to achieve desired shock absorption proportions. The outer bearing can further include a compression limiter so as to maintain proper tolerances between the outer bearing inner surfaces and the inner bearing surfaces in confronting relation therewith as the outer bearing is loaded. In this manner, the inner bearing maintains its freedom of movement despite the compressive loading that is being borne by the outer bearing, as will be described more fully hereinafter.

In one form, the artificial disc includes a central ball as the enlarged, central bearing portion with an annular body of the outer bearing extending thereabout. The upper and lower load bearing surfaces or surface portions of the outer bearing body preferably do not project axially as far toward the upper and lower vertebrae as the ball surface portions such as by having a larger radius of curvature than the radius of the ball. In other words, the load bearing surface portions have a more gradual curvature than the center bearing surface portions or for that matter they can have a flat configuration. This allows the enlarged ball to seat in the indents in the end plates for positioning the artificial disc securely between the vertebrae while the annular body is also effective in taking up the compressive loading between the upper and lower vertebrae.

In another form, the central bearing portion includes a pair of generally dome-shaped shell members that ride on a generally spherical inner bearing portion integral with the outer bearing portion for sliding thereover. In this regard, the inner bearing portion is integrally connected to the outer bearing portion via a circumferential web wall. The domes or shells are sized relative to the inner spherical bearing portion so that there are gap spaces between the peripheral edges of the domes and the web wall. The web wall positions the outer, annular load bearing portion such that interference with shifting of the domes on the central spherical bearing portion is minimized. Alternatively, snap-fitting the domes in place over the inner ball bearing portion could be employed; however, the above described loose-fitting construction is preferred to minimize binding of the dome shells under compressive load forces. In this manner, the domes can readily slide on the inner ball portion and, at the same time, the vertebral end plates or other vertebral surfaces in engagement with the arcuate surfaces of the domes can also shift with respect thereto to provide a bi-polar device with two interfaces that shift with respect to each other.

By having this bi-polar artificial disc construction, the stress and wear that would otherwise occur in either of the interfaces is decreased as one bearing interface can be shifting when the load on the other becomes too great. Lubricant can be provided between the dome shells and the inner bearing portion to reduce friction and wear therebetween. A seal ring attached adjacent or at the end edge of the shells for being carried therewith minimizes lubrication leakage while allowing the shells to slide over the spherical surface of the inner bearing portion in a low friction manner.

BRIEF DESCRIPTION OF THE DRAWINGS

FIGS. 1F-1H and 1J are directed to various views of a disc device slightly modified over that shown in FIGS. 1A-1E to better conform to the vertebrae;

DETAILED DESCRIPTION OF THE PREFERRED EMBODIMENTS

Figure 1A:
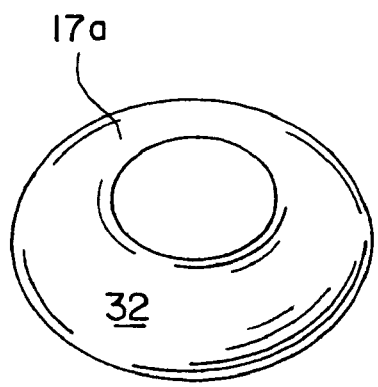
FIGS. 1A-1E are directed to various views of one form of an artificial disc implant device in accordance with the present invention showing an enlarged spherical central bearing and an outer annular bearing.
Figure 1B:
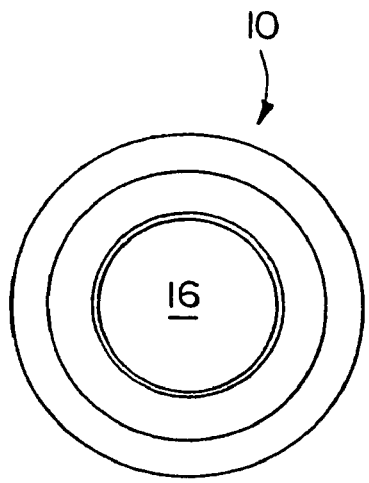
Figure 1C:
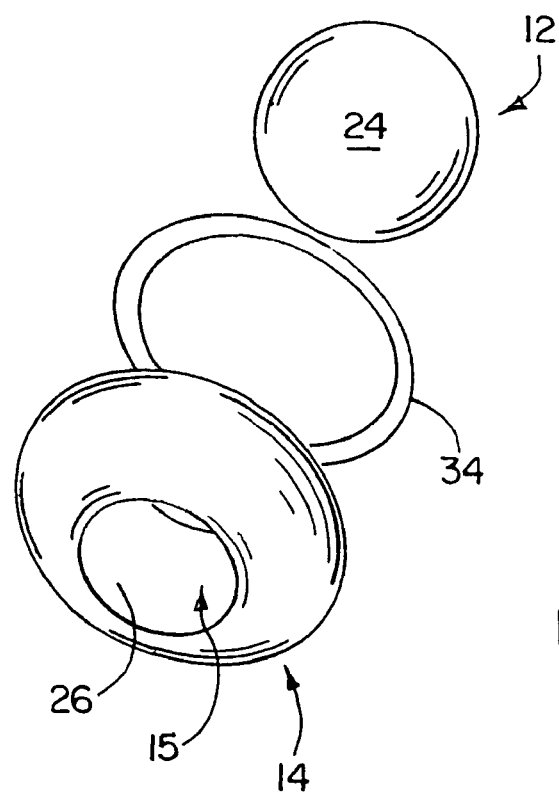
Figure 1D:
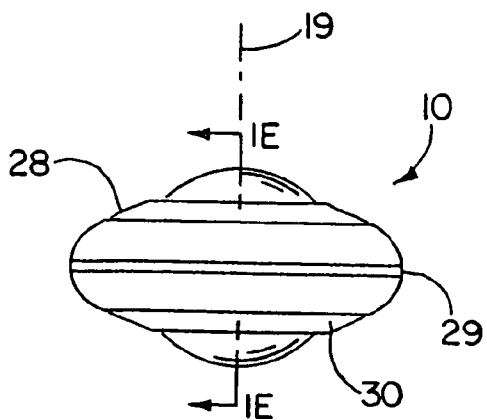
Figure 1E:
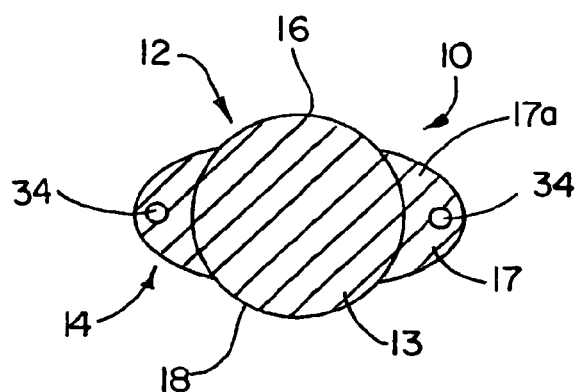
Figure 1J:
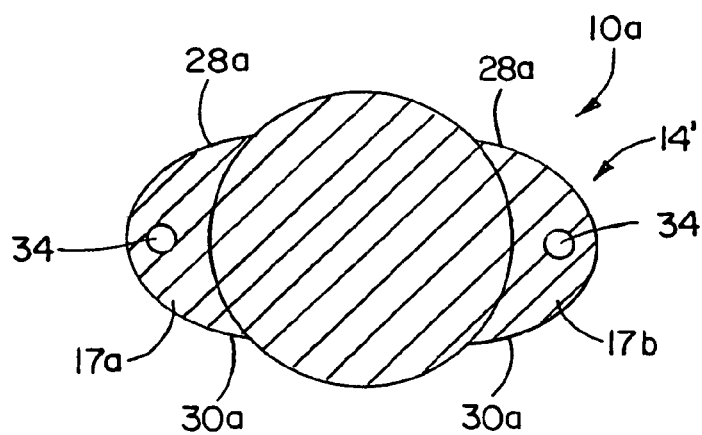
Figure 1F:
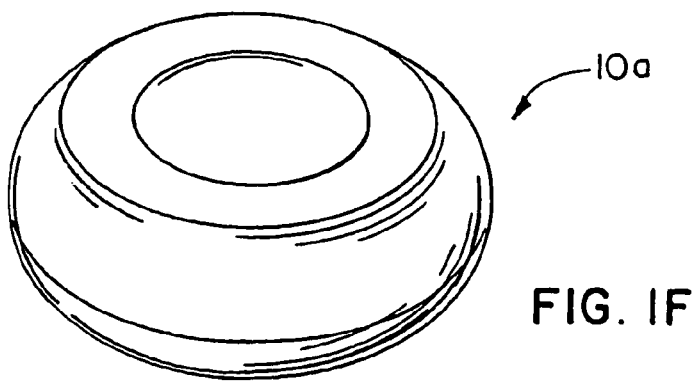
Figure 2A:
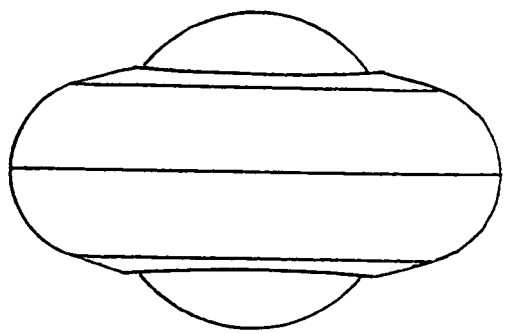
FIGS. 2A-2D are directed to various views of the artificial disc device of FIGS. 1A-1E as implanted between adjacent upper and lower vertebrae.
Figure 2A:
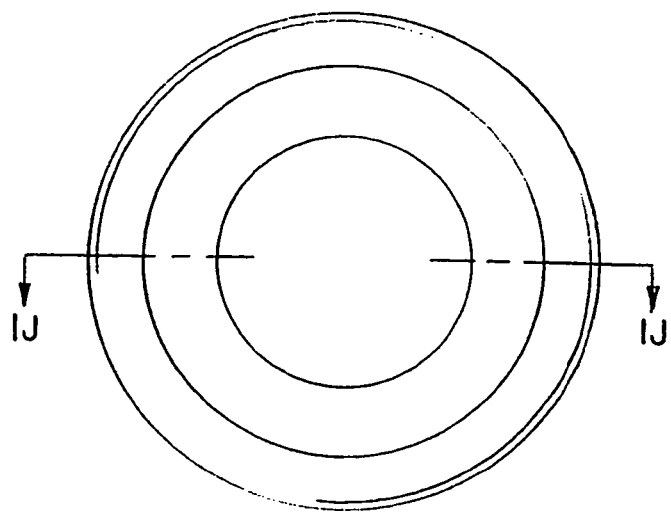
Figure 2A:
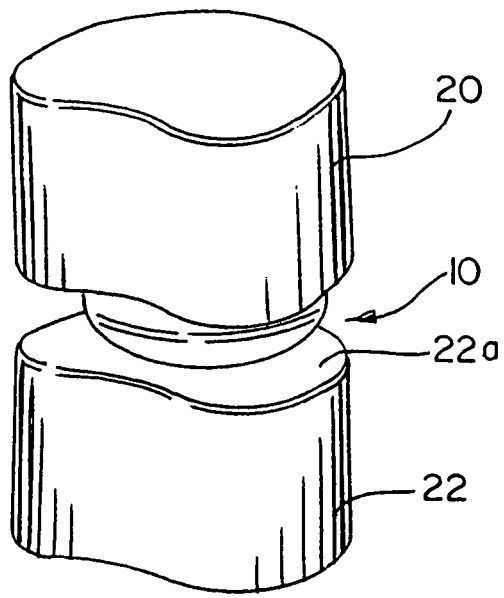
Figure 2B:
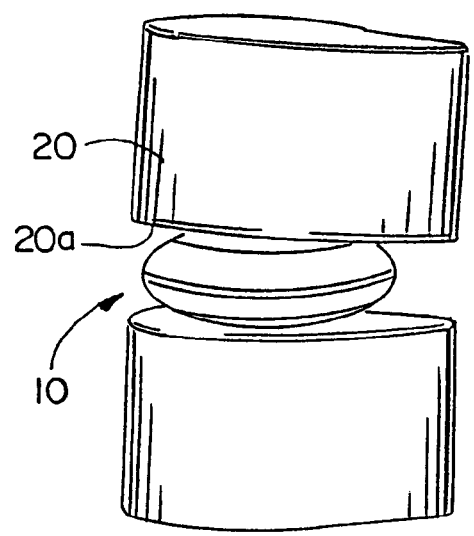
Figure 2C:
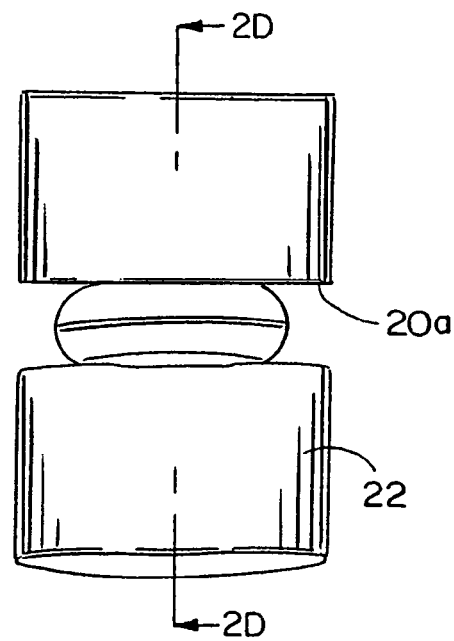
Figure 2D:
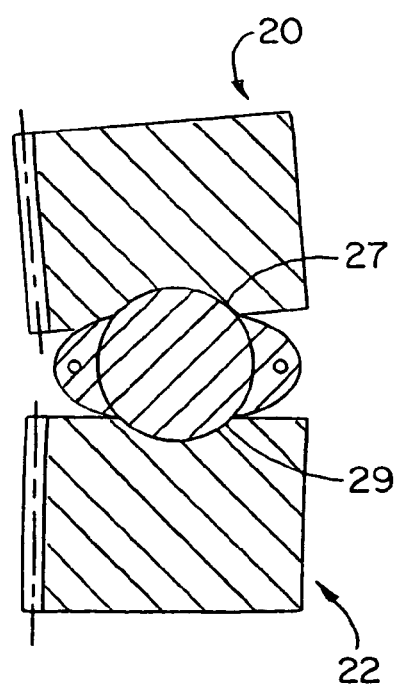

Referencing FIGS. 1A-1E, an artificial disc device 10 is shown which includes an enlarged, central bearing portion 12, and a substantially annular, outer bearing portion 14 having a through opening 15 in which the central bearing portion 12 is disposed. Herein, preferred shapes, configurations and material selections for the inner and outer bearing portions are set forth. However, in each case, these selections are not meant to be limiting as other selections that serve the purpose of the disc implant described herein are also contemplated. Likewise, several embodiments are disclosed that have structural features that can be implemented substantially interchangeably among the disc implants.

In the form illustrated in FIGS. 1A-1E, the central bearing 12 has an axially enlarged body 13 relative to the outer bearing 14 so that it generally includes arcuate surface portions 16 and 18 that project above and below the radially outer bearing portion 14 for engaging in indents in confronting surfaces 20a and 22a of the adjacent upper and lower vertebrae 20 and 22, respectively, for seating the implant 10 therein. In the implant device 10, the central bearing 12 can be in the form of a generally spherical ball such that the surface portions 16 and 18 are part of the outer spherical surface 24 thereof. The annular bearing portion 14 has a generally ring-shaped (e.g. circular, oval or ellipsoidal) body 17 that includes an arcuate inner side surface 26 extending about the opening 15 that faces the ball bearing 12 having generally the same radius of curvature as that of the spherical ball surface 24 so that the ball bearing 12 can substantially freely rotate in the small, concave indents, divots or depressions 27 and 29 formed in the vertebrae confronting surfaces in which the ball 12 seats, as described above and shown in FIGS. 2A-2D. At the same time, the vertebral surfaces 20a and 22a, and particularly the concave indents 27 and 29 formed therein can readily slide over the ball surface 24. The configuration and rotation of the ball bearing 12 allows the spine vertebrae 20 and 22 to substantially undergo the normal range of biomechanical movement such as when the patient is twisting their back and/or bending it in various directions.

When the implanted disc 10 undergoes compressive loading, the outer bearing 14, and in particular the upper and lower surface portions 28 and 30 thereof will substantially maintain the effective spacing between the vertebrae 20 and 22. Thus, in the present artificial disc device 10, the outer ring bearing body 17 shares the loading with the ball bearing body 13 created between the dynamically moving vertebrae 20 and 22 so as to avoid subsidence problems as occurred with prior ball bearing-type devices. Accordingly, in the disc 10, the outer bearing 14 generally will not allow the end plates to subside around the ball bearing 12.

As shown, the curvature of the upper and lower surface portions 28 and 30 of the outer bearing body 17 is more gradual than that of the arc surface portions 16 and 18 of the central ball bearing body 13 to provide it with a doughnut-type configuration. Accordingly, in the device 10, the surface portions 28 and 30 are part of a substantially continuously curved outer ring bearing surface 32 such that they curve around the radially outermost point 29 of the outer bearing body 17 to form an outwardly projecting convex configuration 29 for the outer surface 32 of the annular bearing 14. As such, the surface portions 16 and 18 extend to their greatest spacing at the central section 17a adjacent the central opening 15 of the bearing body 17. At the thickest section 17a, the spacing of the surface portions 16 and 18 is less than the diameter of the ball bearing 12 so that the surface portions 16 and 18 protrude from the opening 15 to extend above and below the respective outer bearing surface portions 28 and 30 for engaging in the concave depressions 27 and 29. The gradual curvature of the surface portions 28 and 30 allows the ring bearing 14 to better conform to the general concavity of the vertebral surfaces 20a and 22a including any attached end plates over time. By way of example and not limitation, the ball bearing diameter can be approximately between 6-18 mm and the maximum thickness of the outer bearing section 17a can be approximately 16 mm. Manifestly, these sizes are to be tailored according to the anatomy of the patient being treated.

Referring to FIGS. 1F-1J, artificial disc device 10a is depicted which has a slightly modified wedged or bulged configuration for corresponding outer bearing body 14' thereof. More particularly, as can be seen in the cross-sectional view of FIG. 1J, the outer bearing body 14' has a thickened section 17a and thinner section 17b as measured between the corresponding upper and lower surface portions 28a and 30a with these sections being generally diametrically opposite each other with a smooth transition therebetween. Since the confronting vertical surfaces 20a and 22a will normally be in a non-parallel orientation relative to each other, the section 17a of the disc device 10a will better conform to the area between the surfaces 20a and 22a that are spaced further from each other with the section 17b fitting better in the more confined, closely spaced area between the vertebrae surfaces 20a and 22a allowing the implant device 10a to be tightly fit or wedged between the vertebrae 20 and 22.

With the vertebrae 20 and 22 exerting compressive loading on the artificial disc device 10, the projecting surface portions 16 and 18 of the center ball bearing 12 will securely engage in the indented recesses 27 and 29 in the confronting vertebral surfaces 20a and 22a for seating the ball bearing 12 therein. As the spine moves causing relative shifting of the vertebrae 20 and 22 about the ball bearing 12 with it freely rotating in the recesses 27 and 29 as necessary, further loading is exerted on the device 10, with the surface portions 28 and 30 of the outer annular bearing 14 being effective to share with the ball bearing 12 the compressive loading that is generated between the vertebrae 20 and 22, and which further can act as a shock absorber for the high impact load bearing that may be needed between the vertebrae 20 and 22, such as described hereinafter. In this manner, the present artificial disc device 10 resists both migration by the seating of the central ball bearing 12 as well as avoiding subsidence problems by providing load bearing which is well distributed across a large radially extending surface area of the device 10 as by the device upper surfaces 16 and 28 and lower surfaces 18 and 30. For example, the distance from the central axis 19 of the ring bearing 14 extending through the opening 15 to the outer end 29 can be approximately 12 mm.

While other material selections are possible, it is presently contemplated that the inner ball bearing 12 preferably will be of a harder material than the outer bearing 14 so that the harder ball 12 is more apt to maintain its conformity with and thus stay seated in the indents 27 and 29 in the surfaces 20a and 22a. In this regard, the ball 12 can be of a biocompatible material including titanium or metallic material such as stainless steel, while the ring bearing 14 can be of a material of a lower modulus of elasticity such as plastic material, e.g polyethylene, so as to have some resilience under compressive loading forces.

With a plastic outer bearing 14, a support hoop 34 of a harder material than that of the outer bearing 14 such as of metal material similar to that of the ball bearing 12 can be embedded therein. Generally, the hardness of the ball bearing 12 and the hoop 34 will both be greater than the outer bearing 14, although they may not be the same as each other. For example, the hoop 34 can be of a hard metal material whereas the center bearing 12 can have a hardness similar to the human bone. To this end, the plastic outer bearing 14 can be a molded component of the artificial disc device 10. As such, the metal support hoop 34 can be molded in situ in the outer ring bearing 14. The support hoop 34 serves as a compression limiter to resist deformation of the resilient plastic ring bearing 14 due to the compressive loading generated between the vertebrae 20 and 22 so that it is better able to maintain its configuration despite the stresses exerted thereon. In addition, the hoop 34 also resists shear forces generated by spinal movements for reducing such forces in the resilient material of the outer bearing 14.

Alternatively, outer bearing body 17 can have an inner core portion that is of different and softer material than that of the harder outer portion so that the annular bearing 14 has improved shock absorbing properties for high force impacts on the artificial disc 10 with the harder outer layer minimizing wear on the bearing 14. For example, the wear layer can be of hard polyethylene material with the inner cushion material of the bearing body 17 being of a softer polymeric or elastomeric material. In another alternative, the body 17 can include a hollowed inner portion that is filled with liquid or gel or other elastic material, e.g. Hydrogel and/or polyurethane, for shock absorption purposes.

FIGS. 3A-3D and 5A-5E are directed to alternative artificial disc devices 36 and 38, respectively. The disc devices 36 and 38 are of similar construction as each include a central bearing portion 39 formed from two opposing shells 40 and 42 having a generally dome-shaped configuration riding on a central or inner, spherical ball bearing portion 44 that can be formed integrally with a body 43 of radially enlarged bearing 46 including outer bearing portion 45 thereof. Opposite upper and lower annular arcuate spaces 43a and 43b are formed in the body 43 separating the bearing portions 44 and 45 by a distance greater than the thickness of the shells 40 and 42 so that respective shell end portions 47 and 49 fit therein allowing the dome shells 40 and 42 to slide on the ball bearing portion 44.

Other differences in the construction of the bearing 46 of the devices 36 and 38 relates to the plan configuration of the outer bearing portion 45. The devices 36 and 38 have their bearing portion 45 provided with a pair of lobe sections 48 and 50 that extend in a continuously curved path about the majority of their peripheries until the lobe perimeters meet at their juncture formed at a recessed area 52 therebetween. In this manner, the plan shape of the lobed bearing 46 more closely approximates that of the vertebrae 20 and 22 between which the devices 36 and 38 are implanted. Ring bearing 14 could be provided with a similar lobed plan configuration. Manifestly, the outer bearings 14 and 46 can be formed with other configuration, e.g. oval in plan, so as to be more closely match that of the intervertebral space in which they are to be implanted.

Another difference resides in the configurations of load bearing surface portions 54 and 56 of the bearing 46 generally corresponding to the load bearing surface portions 28 and 30 of the bearing 14. In contrast to the curvature of the surfaces 28 and 30 of the ring bearing 14, the surfaces 54 and 56 are shown as having a generally flat, parallel configuration so that the bearing body 43 has more of a disc or plate-like configuration. Generally, however, some curvature on these bearings surfaces 54 and 56 will be desirable although perhaps modified from that shown for bearing surfaces 28 and 30 for the implant 10. The surfaces 54 and 56 are provided with a spacing smaller than that of the diameter of the central bearing portion 44 and thus of the central bearing assembly 39 with the dome shells 40 and 42 thereon so that they project above and below the respective surfaces 54 and 56. In this manner, the dome shells 40 and 42 are able to seat in indents 27 and 29 in the vertebral surfaces 20a and 22a like the bearing ball surface portion 16 and 18. To this end, the shells 40 and 42 can be of harder material than that of the bearing body 43, and particularly the ball bearing portion 44 thereof. Accordingly, similar to the ball bearing 12, the dome shells 40 and 42 can be of a ceramic material or a stainless-steel metal, titanium or alloys thereof, whereas the ring bearing 46 is preferably of a plastic or polymer material such as polyethylene to provide it with stiffness and resiliency under compressive loading. The bearing 46 could also be of like material to that of the dome shells 40 and 42 for higher load bearing capacity.

Figure 3A:
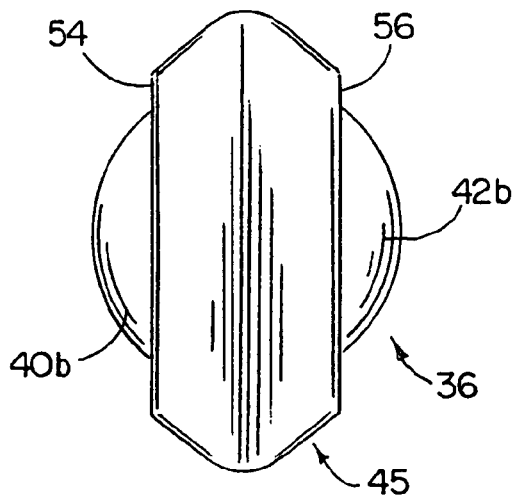
FIGS. 3A-3D are directed to various views of an alternative artificial disc in accordance with the present invention showing a pair of dome shells that ride on an inner, spherical bearing portion integral with the outer annular bearing portion.
Figure 3B:
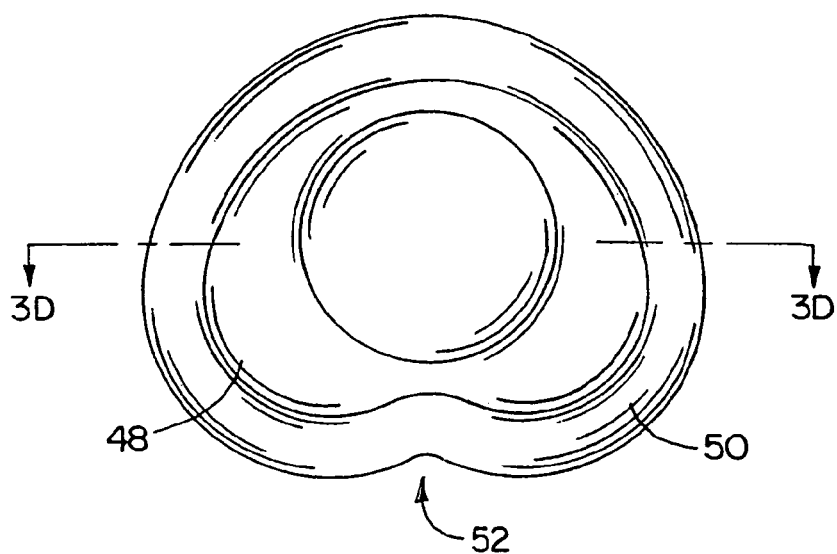
Figure 3D:
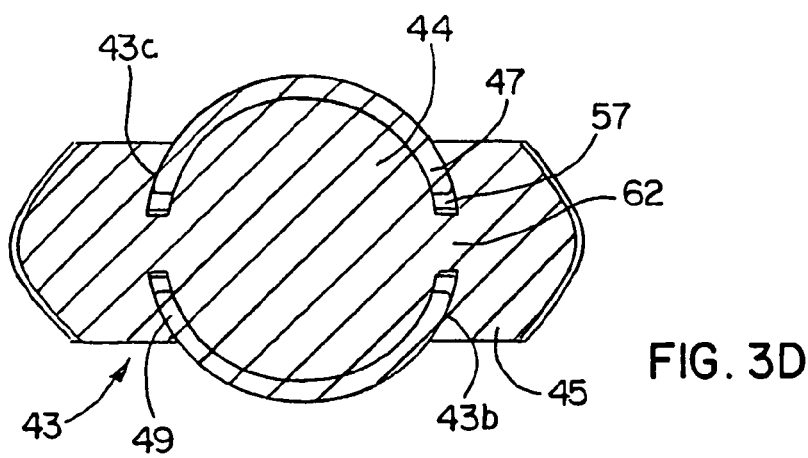
Figure 3C:
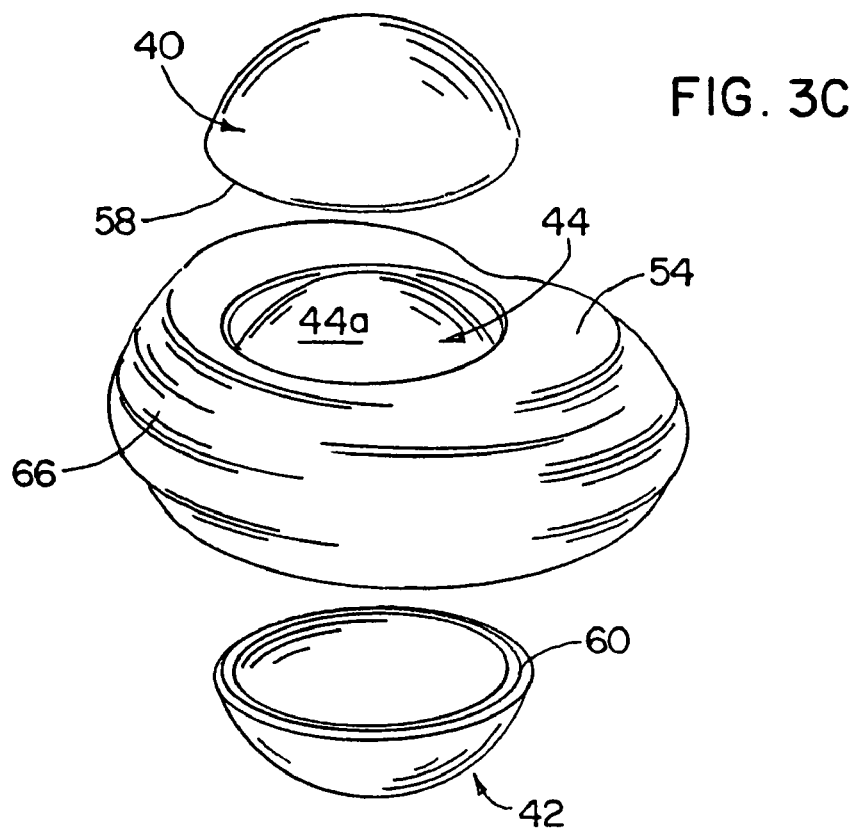
Figure 5A:
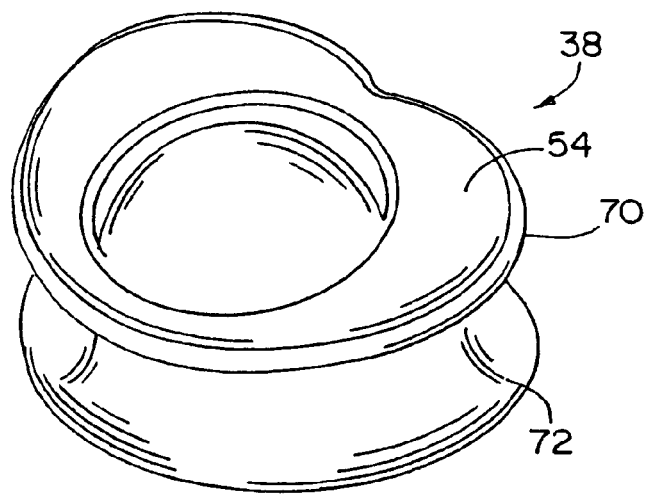
FIGS. 5A-5E are directed to various views of an artificial disc device similar to that shown in FIGS. 3A-3D except having a circumferential groove extending about the periphery of the outer bearing portion.
Figure 5D:
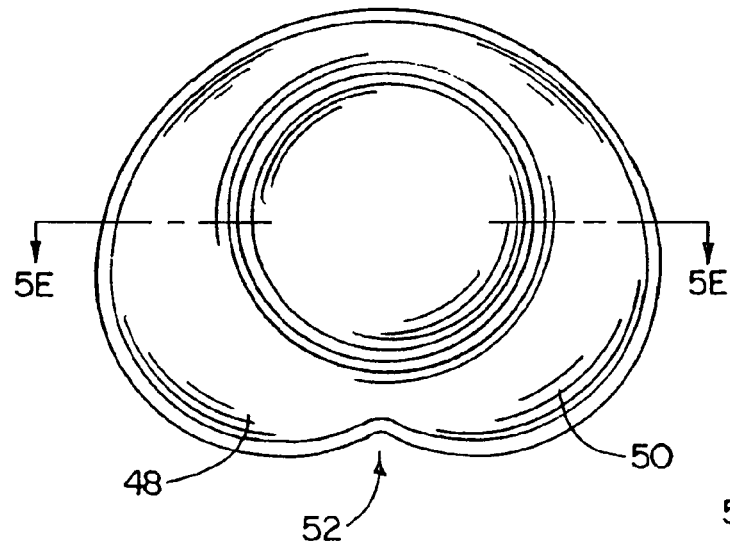
Figure 5B:
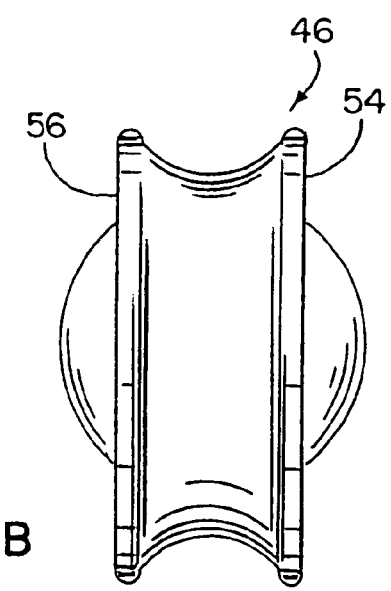

The dome shells 40 and 42 are sized relative to the spherical bearing portion 44 such that there are gap spacings 57 between peripheral end edges 58 and 60 of the respective shells 40 and 42 at their largest diameters and web wall 62 in the bearing 46, as best seen in the cross sectional views of FIGS. 3D and 5D. Accordingly, the diameter across the end edges 58 and 60 of the dome shells is less than the diameter of the ball bearing portion 44. In use, the dome shells 40 and 42 can slide to take up these spaces 57.

The web wall 62 extends laterally or radially and centrally from the ball bearing portion 44 to the annular load bearing portion 45 that extends about the ball bearing portion 44 on which the shells 40 and 42 ride. The circumferential web wall 62 extends radially for a sufficient distance, such that the outer bearing portion 45 is spaced from the ball bearing portion 44 to provide recesses 43a and 43b large enough to allow the dome edges 58 and 60 to slide into engagement with the web wall 62 without encountering interference from the annular load bearing portion 45 of the bearing 46.

In the device 38, the annular bearing portion 45 includes a radially inner surface 51 that extends generally axially or tangentially to outer spherical surface 44a of the inner bearing portion 44, albeit spaced slightly therefrom via web wall 62. In this manner, the corresponding spaces 43a and 43b in the body 43 of the device 38 are enlarged over those in device 36 such that overhanging portions of the bearing portion 45 that can be compressed against the dome shell portions 47 and 49 and potentially cause binding in the spaces 43a and 43b are avoided.

With the above-described construction, the artificial disc devices 36 and 38 have a bi-polar construction in that relative movement between the vertebrae 20 and 22 and the dome shells 40 and 42 can occur along with relative movement between the dome shells 40 and 42 and the ball bearing portion 44. Generally, the smooth surface interface between inner surfaces 40a and 42a of the respective shells 40 and 42 and the outer surface 44a of the ball bearing portion 44 will have a lower coefficient of friction therebetween than that between outer surfaces 40b and 42b of the respective shells 40 and 42 and the indents 27 and 29 in the vertebrae surfaces 20a and 22a. Thus, there will be some differential shifting that can occur with the moving components of the devices 36 and 38 such that generally the domes 40 and 42 will more readily shift along the ball bearing portion 44 prior to shifting of the dome shells 40 and 42 with respect to the vertebrae 20 and 22. Such differential articulation keeps wear between the higher coefficient of friction surfaces to a minimum as sliding can preferentially occur between the smooth inner arcuate surfaces 40a and 42a of the respective shells 40 and 42 and the outer surface 44a of the ball bearing portion 44. Alternatively, if the coefficient of friction is lower between the vertebrae surface concave indents 27 and 29 and the shell outer surfaces 40b and 42b, then of course shifting will preferentially occur at this interface of the disc devices 36 and 38 keeping wear at the higher friction interface between the shell inner surfaces 40a and 42a and ball surface 44a to a minimum. Of course, as the spine is undergoing various dynamic forces during the movements it is required to undertake, oftentimes both interfaces of the bi-polar devices 36 and 38 will be shifting simultaneously to provide the spine with the necessary biomechanics while also keeping undue wear on the disc devices 36 and 38 to a minimum.

Figure 4A:
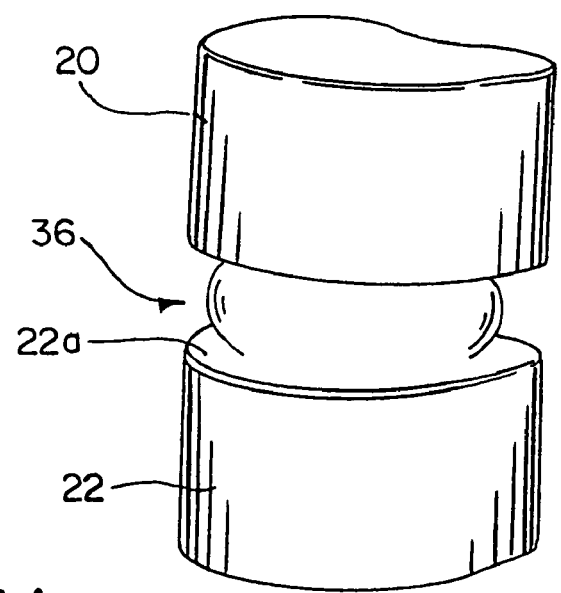
FIGS. 4A-4D are directed to various views of the artificial disc device of FIGS. 3A-3D implanted between upper and lower vertebrae.
Figure 4B:
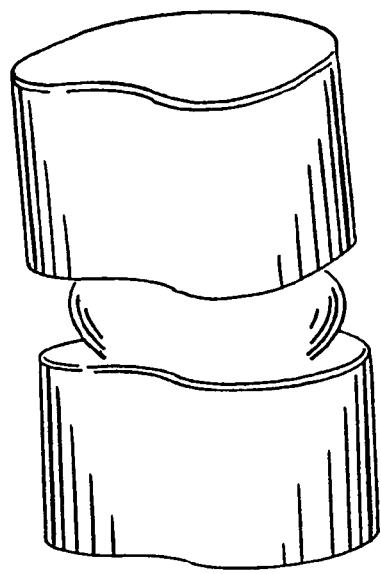
Figure 4C:
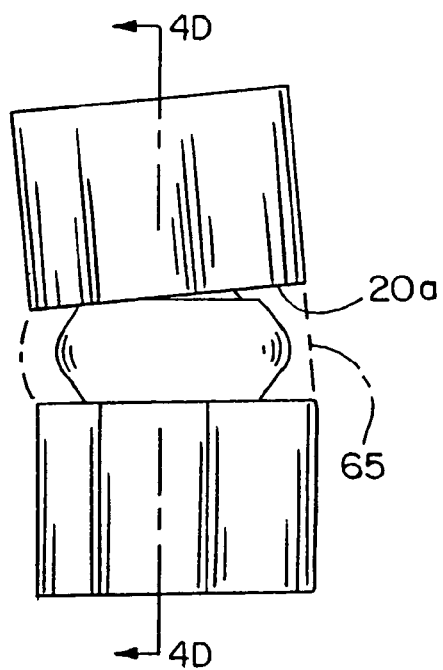
Figure 4D:
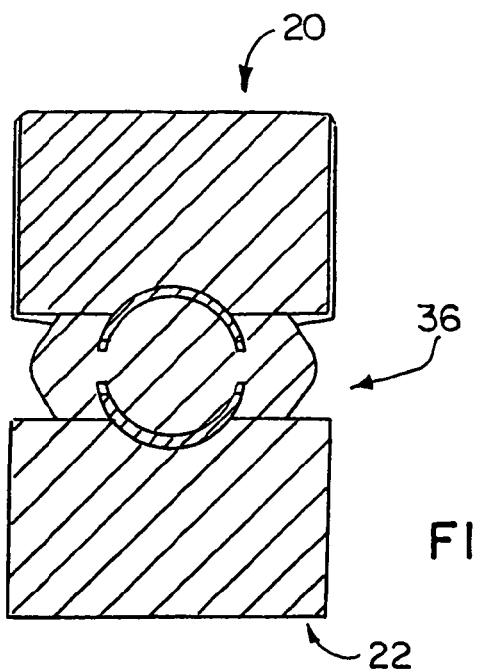

FIGS. 4A-4D illustrate the lobed artificial disc device 36 implanted between the adjacent upper and lower vertebrae 20 and 22. In the view of FIG. 4C, the disc device 36 is employed with the annulus 65 kept intact, and in the other view, the annulus 65 is removed with the disc device 36 implanted. To maintain the annulus 65, the disc device 36 is inserted through an incision in the annulus 65 which may be repaired once the device 36 is implanted. In this instance, the device 36 reinflates the annulus 65 keeping it taut and relieves the compressive loading on the annulus 65. The other artificial disc devices described herein can be employed in a like manner to that of device 36.

Figure 5C:
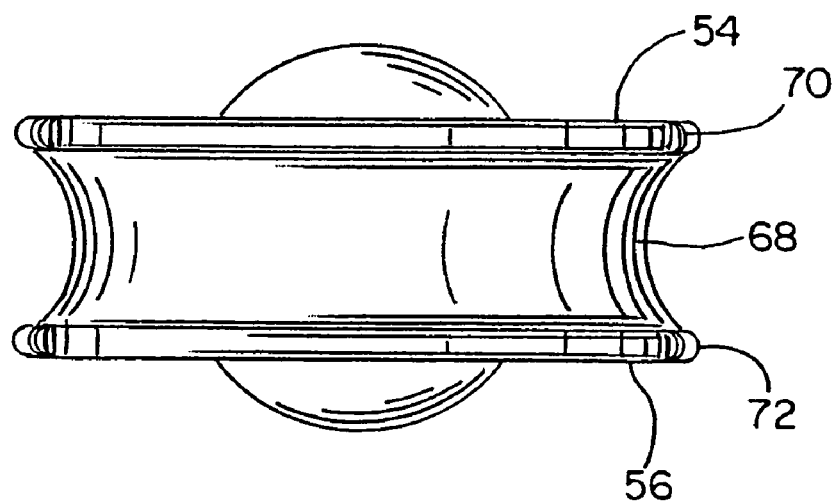
Figure 5E:
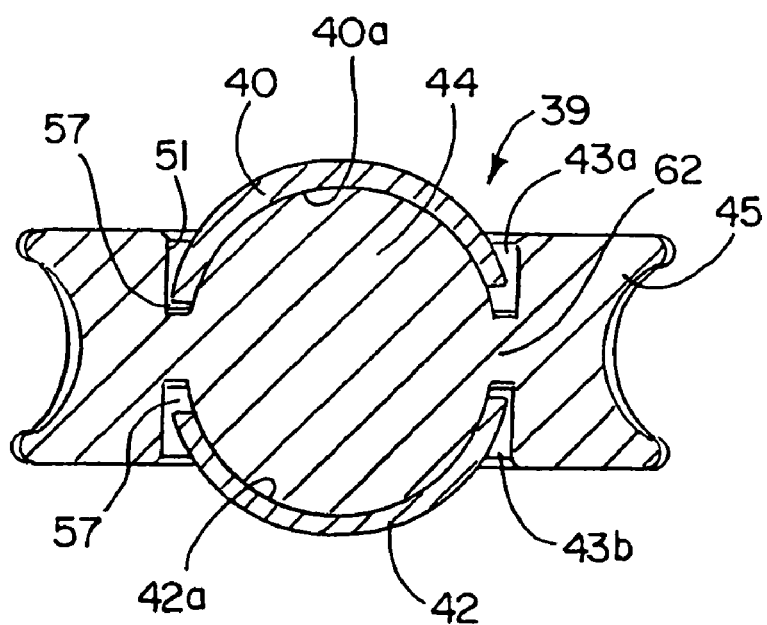
Figure 6A:
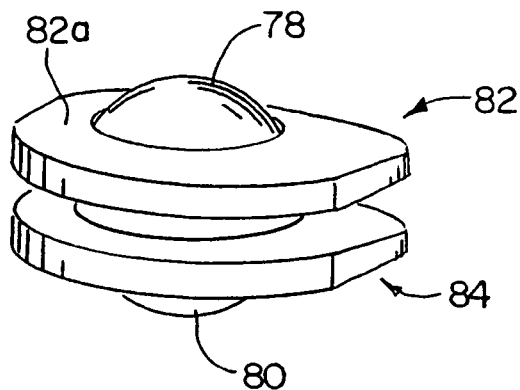
FIGS. 6A-6F are directed to various views of another artificial disc device in accordance with the present invention showing a pair of outer, annular bearings that fit about an enlarged, central spherical bearing.
Figure 6B:
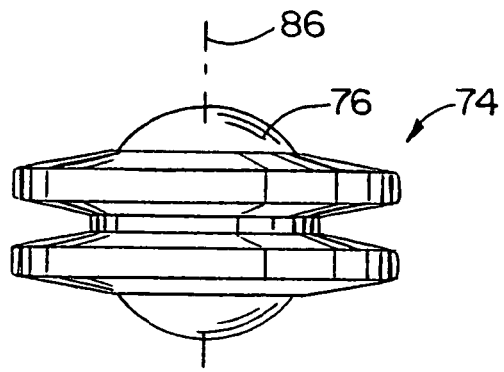
Figure 6C:
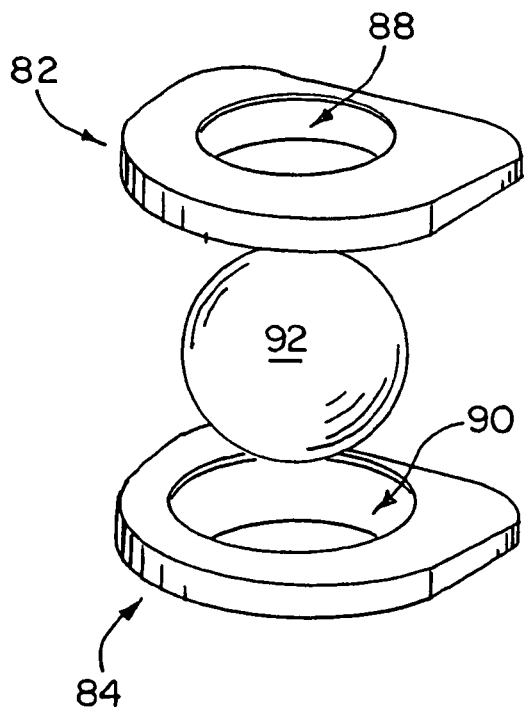
Figure 6D:
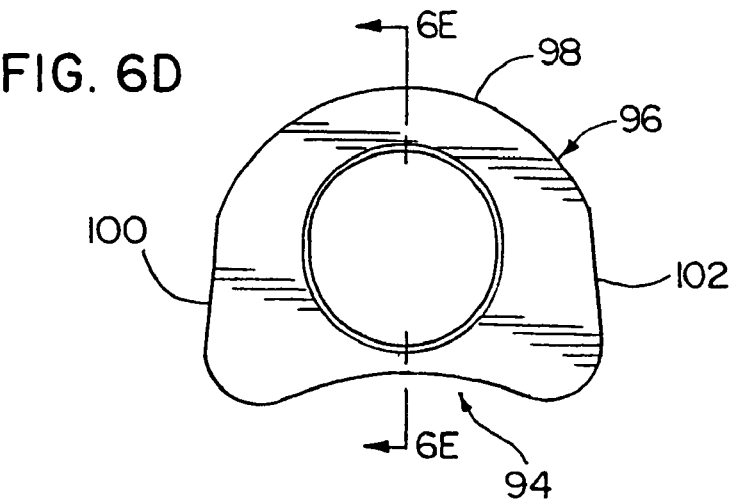
Figure 6E:
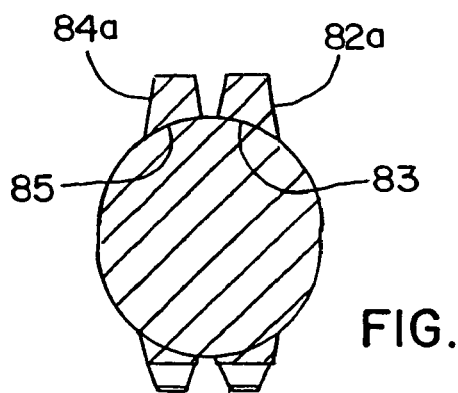
Figure 6F:
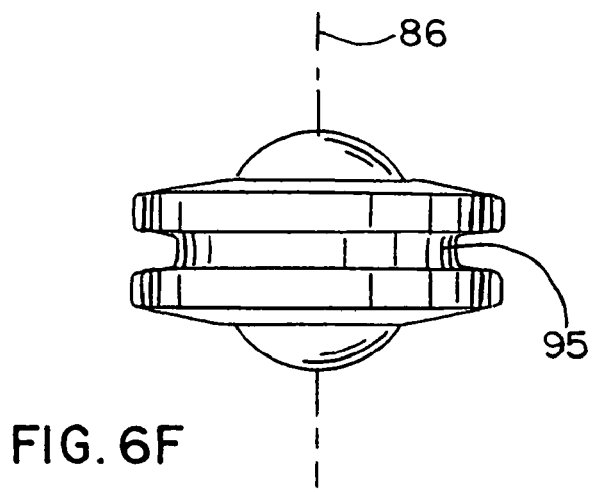

The annular load bearing body portion 45 of the device 36 has an outer peripheral surface 66 (FIG. 3C) with a generally convex configuration similar to the convex curved configuration at the corresponding radially outer location of the outer annular bearing 14. In contrast, the corresponding surface 68 of the load bearing portion 46 of the device 38 shown in FIG. 5C has a grooved or concave configuration to form thinned upper and lower flange rims 70 and 72 thereof. The above-described construction for the bearing 46 as shown in FIG. 5C provides it with greater flexibility as the flanges 70 and 72 are better able to flex toward each other under compressive loading and thus are optimized from a shock absorption standpoint. In particular, by having the flanges 70 and 72 extending around the entire circumference of the bearing 46, compressive loads taken locally by the bearing 46 such as due to bending of the spine in a particular direction will cause the portions of the flanges 70 and 72 thereat to flex toward each other about the concave peripheral surface 68 while the remainder of the disc 46 including the unloaded portions of the flanges 70 and 72 will remain substantially undeformed. Once this loading is removed, the bent portion of the flanges 70 and 72 can resiliently flex back to their illustrated substantially undeformed configuration. In this manner, the flanges 70 and 72 better permit directional deformation of the bearing 46.

Optionally, upper and lower annular layers including the flanges 70 and 72 can be provided of harder material than a more flexible core material of the bearing body 43 for optimized wear resistance at the interfaces with the vertebral surfaces 20a and 22a and also for improved shock absorbing properties for the device 38a. For instance, the wear layers can be of hard polyethylene while the core of the body 43 would be of more flexible, e.g. elastomeric, cushioning material.

Referring next to FIGS. 6A-6F, another artificial disc device 74 in accordance with the invention is illustrated. The artificial disc device 74 is similar to the device 10 of FIGS. 1A-1E in that it includes a central ball bearing 76 such as of ceramic material or stainless steel or titanium metal and alloys thereof or having carbon fiber or other biocompatible materials therein and including projecting arc surface portions 78 and 80 for seating in the indents 27 and 29 in the vertebral surfaces 20a and 22a, as previously described. The device 74 is modified over device 10 in that rather than having a doughnut shaped bearing 14, the device 74 includes a pair of annular plates or discs 82 and 84 such as of a metallic material vertically spaced along central axis 86 that extends through the central openings 88 and 90 formed in the respective discs 82 and 84 in which the ball bearing 76 is received. As shown, the disc openings 88 and 90 are of a maximum diameter that is slightly less than that of the diameter of the ball bearing 76 such that when the arcuate surfaces 83 and 85 about the openings 88 and 90 are in close fit with the outer ball surface 92 and the discs 82 and 84 are in a generally parallel orientation, the discs 82 and 84 will be spaced by a gap 94 therebetween.

With the device 74 loaded and the confronting vertebral surfaces 20a and 22a engaging and pushing on the discs 82 and 84, they will shift and pivot relative to each other and axis 86 closing the gap 94 at certain locations thereabout and opening it at others. As such, it is the upper surface 82a and lower surface 84a of the respective upper and lower discs 82 and 84 that are the major load bearing surfaces for the device 74. As shown, these surfaces 82a and 84a can be contoured so that the respective discs become thicker as extending from the periphery toward the respective openings 88 and 90 of the discs 82 and 84.

In an alternative form, a resilient and flexible cushioning material 95 can be attached between the discs 82 and 84. The material 95 will keep the unloaded discs 82 and 84 in the illustrated, generally parallel orientation, but also allow them to undergo relative shifting under compressive loading. In this regard, the material 95 is selected so that it can resiliently expand and contract as the discs 82 and 84 shift and tilt or pivot with respect to each other. Alternatively, the unloaded discs 82 and 84 could be canted to a non-parallel orientation relative to each other to provide the disc device 74 with a wedged configuration similar to the previously-described device 10a.

Accordingly and as described above, as the spine and particularly the vertebrae 20 and 22 exert compressive loading on the discs 82 and 84, they can shift relative to one another so they are better able to conform to the position of the vertebrae 20 and 22 as they shift with spine movement. For example, if the patient bends anteriorly, the upper disc 82 can tilt relative to the axis 86 so the gap spacing 94 between the discs 82 and 84 can be greater at the rear portion than at the forward portions thereof. In a like manner, if the patient bends their spine posteriorly, then the upper disc 82 can pivot about axis 86 such that the gap spacing 94 can be greater at the forward portions relative to the spacing at the rear portions. In each instance described above, there will usually be some tilting of the lower disc 84 as well although not to the same degree as that of the upper disc 82 so that their tilting movements relative to the axis 86 generally will correspond to that of the upper and lower vertebrae 20 and 22 and the surfaces 20a and 22a thereof relative to the axis of the spine.

The discs 82 and 84 can have a plan configuration akin to that of the lobed bearing 46, or alternatively they can be oval or ellipsoidal. As shown in the plan view of FIG. 6D, the configuration of the discs 82 and 84 includes a larger recessed or concave area 94 as compared with the corresponding recess area 52 of the ring bearing 46. Further, the curvature of the remainder of the disc periphery 96 varies from a convexly curved portion 98 opposite the recessed area 94 to straighter opposite sides 100 and 102 on either side of the recessed area 94.

Figure 7A:
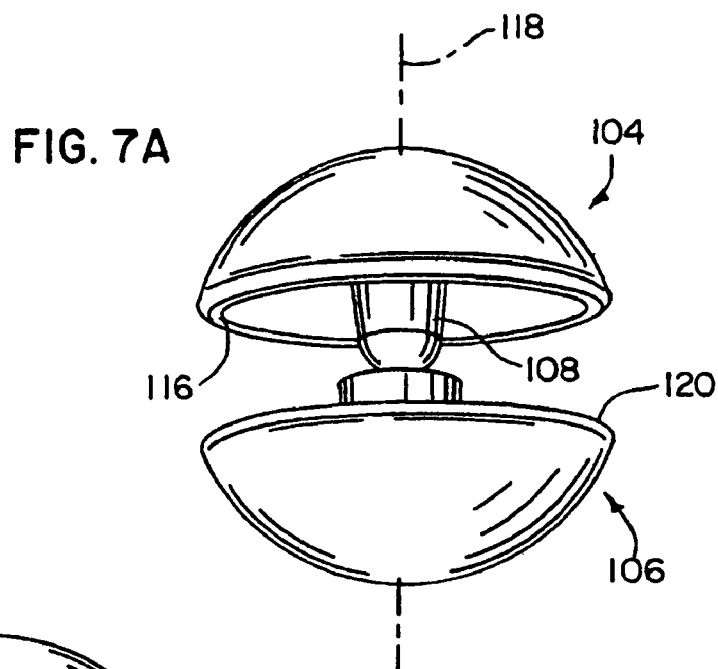
FIGS. 7A-7C are directed to various views of an alternative construction of the central bearing showing opposing dome shells, one having a central post projection and the other having a central hub.
Figure 7B:
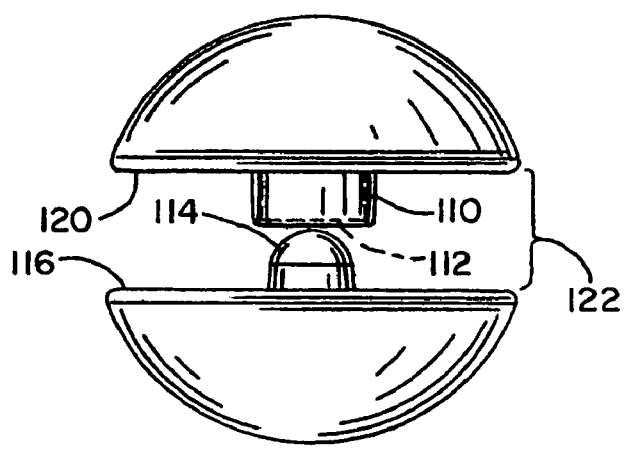
Figure 7C:
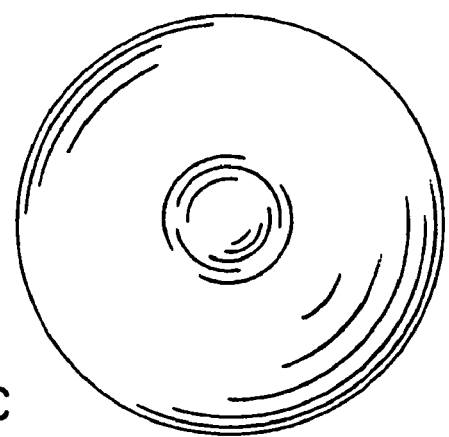

Turning to FIGS. 7A-7C, an alternative construction for the central bearing 39 is shown. In this version, a pair of opposing domes 104 and 106 are provided which ride on an inner bearing portion 107 similar to previously-described ball bearing portion 44, albeit modified to accommodate the projecting post 108 and hub 110, which are described below.

The hub 110 can have a recess 112 which can engage against the distal curved end 114 of the post 108 to resist the compressive forces that otherwise would push the dome shells 104 and 106 further toward each other. More particularly, the dome shell 104 has an end edge 116 and the post 108 extends centrally from the shell 104 along axis 118 so that it projects beyond the edge 116. Likewise, the shell 106 includes an end edge 120 beyond which the hub 110 can project along the central axis 118 so that it is in alignment with the post 108. The post 108 and hub 110 have their respective sizes coordinated so that they define a limit at which spacing 122 between the dome shells 104 and 106 cannot be exceeded with the end edges 116 and 120 extending generally parallel to each other. In this manner, unlike the previously described central bearing assemblies 39 that rely on the stiffness or resilience of the polymeric spherical bearing portion 44 to resist compression of the dome shells 40 and 42, the dome shells 104 and 106 which are preferably of a harder material such as metal employ the cooperating integral post 108 and hub 110 for limiting the maximum compression that can occur therebetween. As is apparent, under normal conditions, the post 108 and hub 110 will be spaced or only lightly engaged so that they do not bear the loads generated between the vertebrae 20 and 22.

Figure 8A:
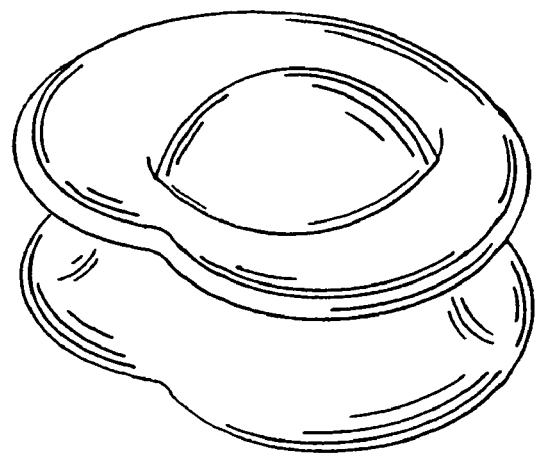
FIGS. 8A-8E are directed to various views of an artificial disc device including the dome shells of FIGS. 7A-7C projecting into an opening formed in the inner bearing portion.
Figure 8B:
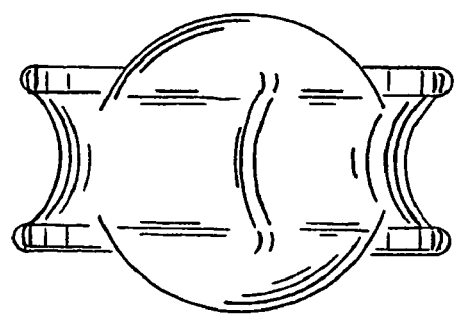
Figure 8C:
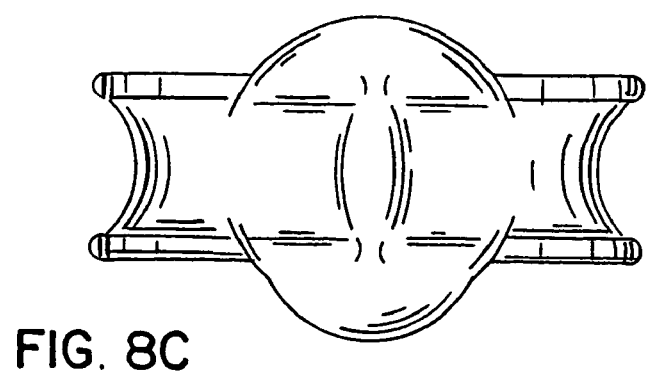
Figure 8D:
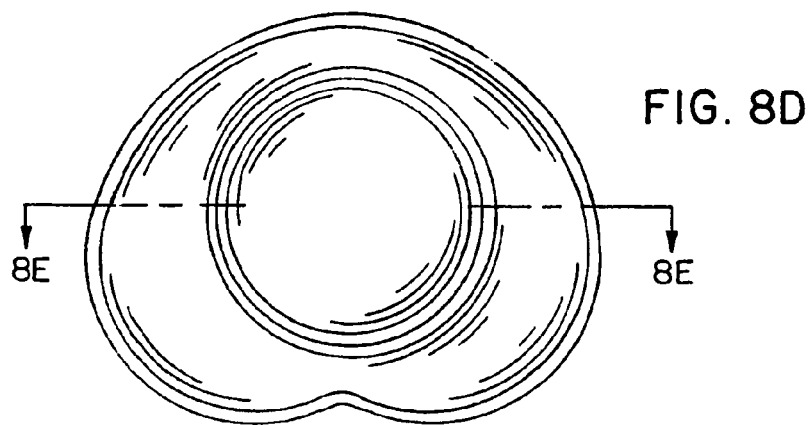
Figure 8E:
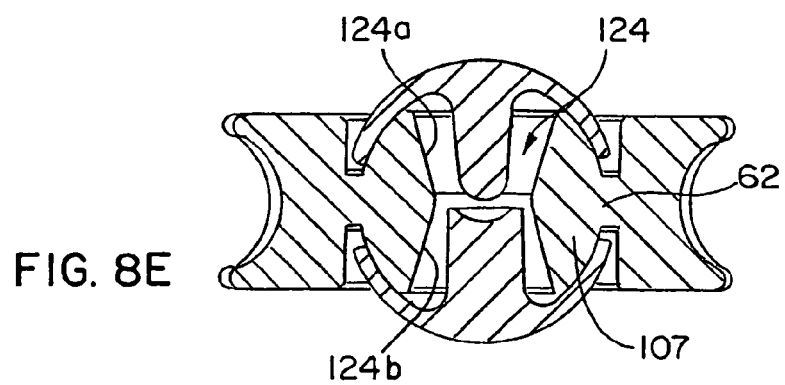

As mentioned above and referencing FIGS. 8A-8E, the central or inner bearing portion 107 is modified so that the post 108 and hub 110 can project therethrough. As seen in the cross-sectional view of FIG. 8E, the bearing portion 107 has an axial through opening 124 having reversely configured upper and lower frustoconical surface portions 124a and 124b into which the post 108 and hub 110 extend, respectively. The surface portions 124a and 124b taper from the largest size of the opening 124 at the dome surfaces to the smallest size of the opening 124 at the center of the ball bearing portion 107. This provides the domes 104 and 106 with freedom of movement about the ball bearing portion 107 allowing the post 108 and hub 110 to rock back and forth until the dome ends 116 and 120 engage the web wall 62 without encountering interference from the surface portions 124a and 124b, respectively.

Figure 9:
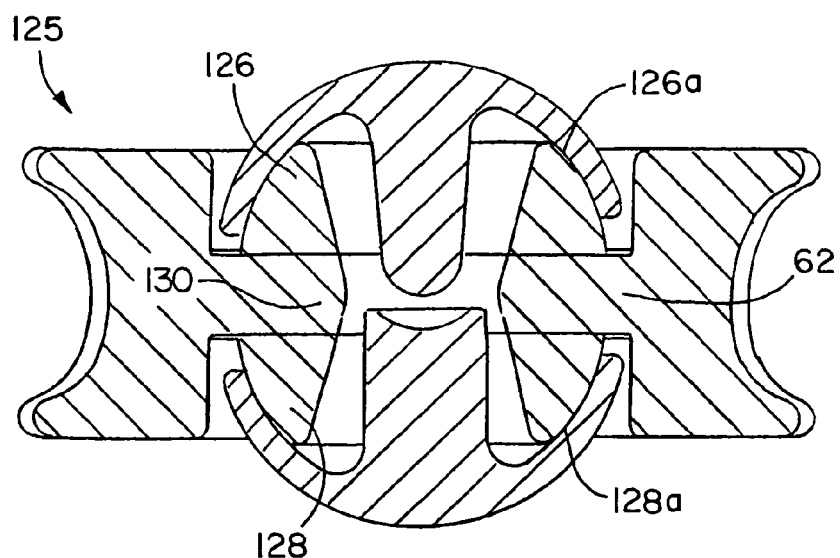
FIG. 9 is a cross-sectional view of an alternate form of the artificial disc device of FIGS. 8A-8E showing a pair of inner bearing rings on which the respective dome shells ride with a cushion web wall therebetween.

In FIG. 9, a further variation of the central bearing assembly shown in FIGS. 8A-8E is illustrated. In this version of an artificial disc device 125, instead of having the apertured central bearing portion 107 that is integrally connected to the web wall 62, upper and lower inner bearing rings 126 and 128 are provided supported by an inner extension 130 of the web wall 62 that extends therebetween. The rings 126 and 128 each have an outer arcuate bearing surface 126a and 128a on which the dome shells 104 and 106 ride. The rings 126 and 128 can also translate along the web wall 62 to provide for lateral movement of either or both dome shells 104 and 106 during articulation of the spine such as when the patient bends their spine in flexion or extension. In this manner, the device 125 provides for an even greater range of motion than the previously described devices as there are now three shifting interfaces including the innermost interface between the rings 126 and 128 and web wall 62 enabling the dome shells 104 and 106 to reciprocate therealong. At the same time, the shells 104 and 106 may be rotating in the indents 27 and 29 and rotating about the rings surfaces 126a and 128a, such as in the previously-described devices. For wear resistance, the rings 126 and 128 can be of a hard polyethylene material while the web wall 62 is preferably of a more flexible or pliant material for shock absorption purposes. For sliding of the rings 126 and 128 on the web wall 62, it can be coated with a harder material or have washers of metallic or a like hardness material attached to upper and lower surfaces thereof to reduce the friction coefficient with the rings 126 and 128 sliding thereon.

Referring next to FIGS. 10A-10H, an alternative artificial disc implant device 132 is illustrated in which there is an enlarged, central bearing member 134 and an outer bearing member 136 which share the compressive loads generated between the vertebrae 20 and 22 during typical spine movements. The central bearing member 134 has a post body 138 that is axially elongated such that upper and lower arcuate bearing surfaces 140 and 142 generally extend beyond corresponding upper and lower bearing surfaces 144 and 146 formed on annular body 148 of the outer bearing member 136, similar to the previously-described disc implants herein.

The outer bearing body 148 has a central through opening 150 that is bounded by a cylindrical inner surface 152 in close confronting relation to outer side surface 154 on the post body 138. To provide optimized controlled resiliency of the shape retentive bearing body 148, through apertures 156 can be formed at selected locations extending axially therethrough, as shown in FIG. 10D. These apertures 156 provide an increase in the normal compressibility or coefficient of restitution of the material, e.g. plastic, of the bearing body 148. Based on the position, pattern and/or density of the through apertures 156, the flexibility or compressibility of the body 148 can be increased or decreased in a localized fashion. Of course, these apertures 156 could be employed in the other disc implants and specifically the bodies of the outer bearings thereof in a like fashion. Similarly, the previously-described liquid or gel material, e.g. Hydrogel, used in the outer bearing body 17 could also be provided in the apertures 156 so that they do not extend all the way through the body 138 and instead serve as chambers for the visco-elastic material therein to vary compressibility of the body 148.

Figure 10A:
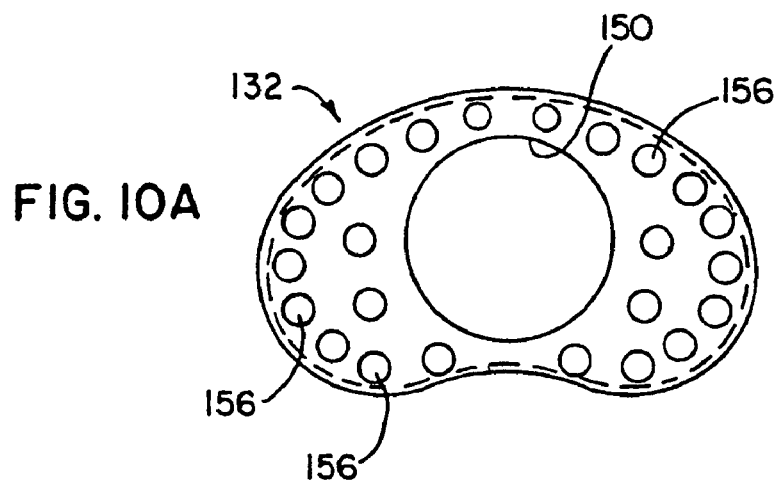
FIGS. 10A-10D are directed to various views of another alternative artificial disc device having an axially enlarged central bearing member and an outer, annular bearing member showing an hour-glass configuration for the central-bearing member and an apertured body of the outer bearing member.
Figure 10B:
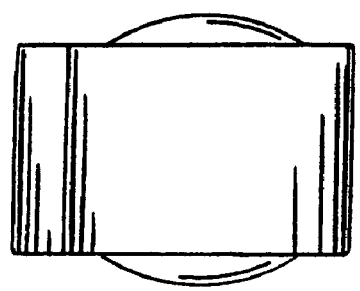
Figure 10C:
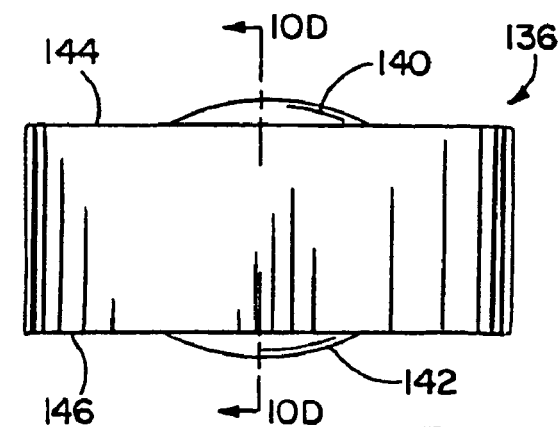
Figure 10D:
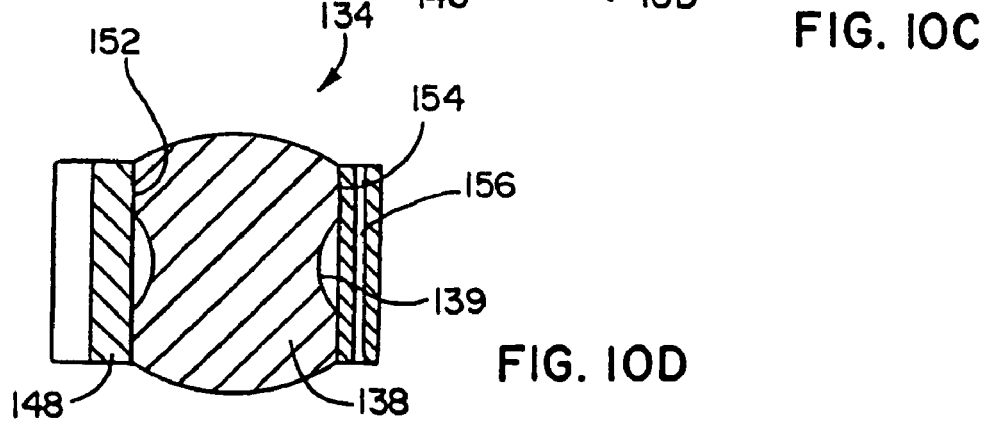
Figure 10E:
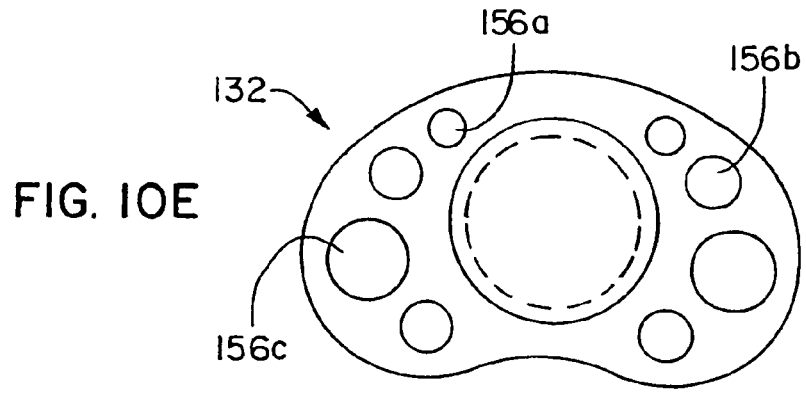
FIGS. 10E-10H are directed to a modified version of the disc device of FIGS. 10A-10D showing different sizes of through apertures formed in the outer bearing member.
Figure 10F:
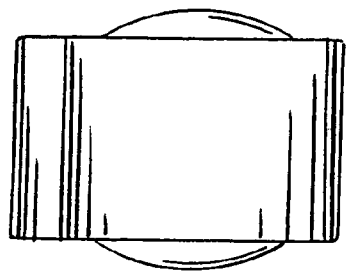
Figure 10G:
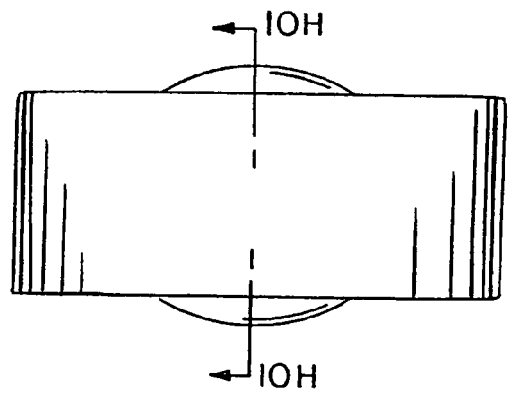

For instance and as shown in the plan view of FIG. 10A, the frequency of the apertures 156 can be increased in a radially outward direction from the central opening 150 to the periphery of the bearing body 148 so that in a like fashion the body 148 can be more easily compressed toward the periphery thereof. Alternatively, the size or diameter of the holes 156 can vary such as by having, for example, smaller size apertures 156a closer to the central opening 150, larger size apertures 156b closest to the radially outer periphery of the body 148, with apertures 15 6c having sizes intermediate those of apertures 156a and 156b generally disposed therebetween, as shown in FIG. 10E. As is apparent, by selective spacing and/or sizing of the aperture 156, the bearing body 148 can be made to be more or less flexibly resilient at precise locations thereabout. In this manner, the bearing body 148 can be stiffer in locations where load bearing is more critical and more compressible at positions were shock absorption is more important. It is also anticipated that the apertures 156 will provide stress relief for the load bearing body 148 so as to increase the life thereof.

Figure 10H:
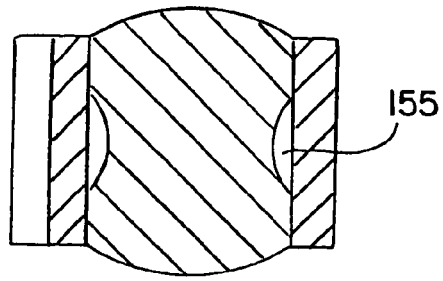

As seen in the cross-sectional views of FIGS. 10D and 10H, the post body 138 preferably is provided with a recess in its surface 154 such as annular groove 139 formed approximately midway along the body length between the bearing surfaces 140 and 142 thereof. By way of this groove 139, there is a gap 155 that is formed between the confronting bearing surfaces 152 and 154. When the resilient body 148 of the outer bearing 136 is compressed, the gap 155 provides space into which the resilient material of the body 148 can deform and expand laterally.

Figure 11A:
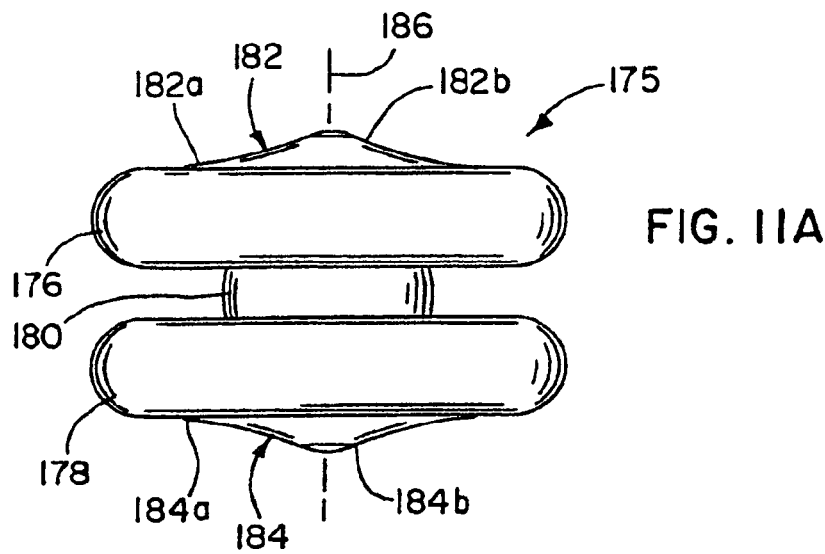
FIGS. 11A-11H are directed to various views of alternative artificial disc devices showing upper and lower bearing members and a load bearing member therebetween.
Figure 11B:
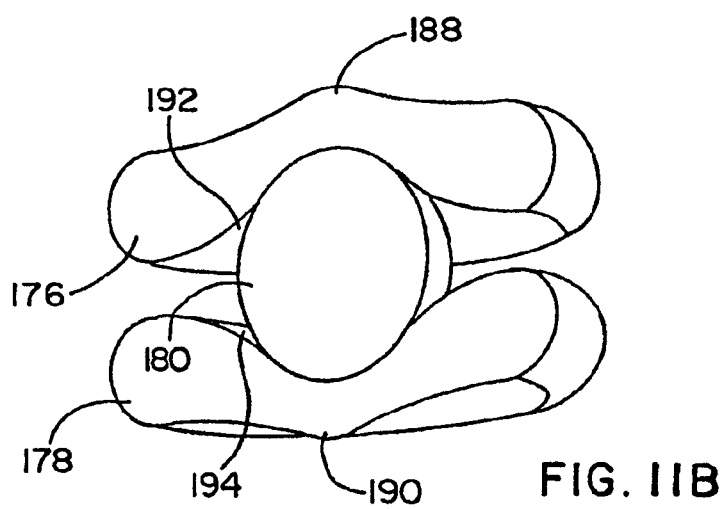
Figure 11C:
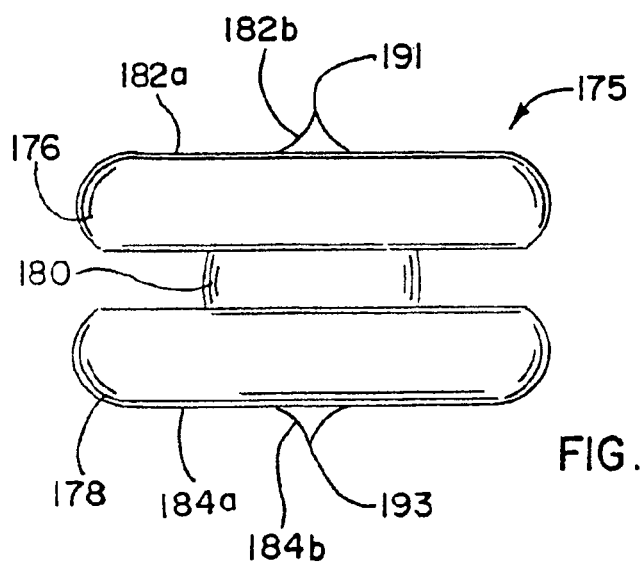
Figure 11D:
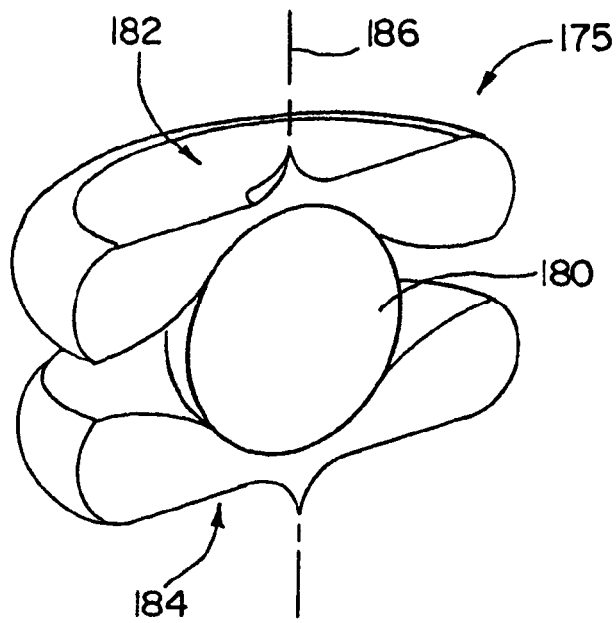
Figure 11E:
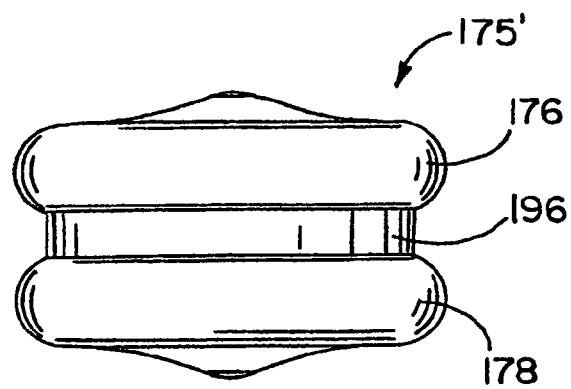
Figure 11F:
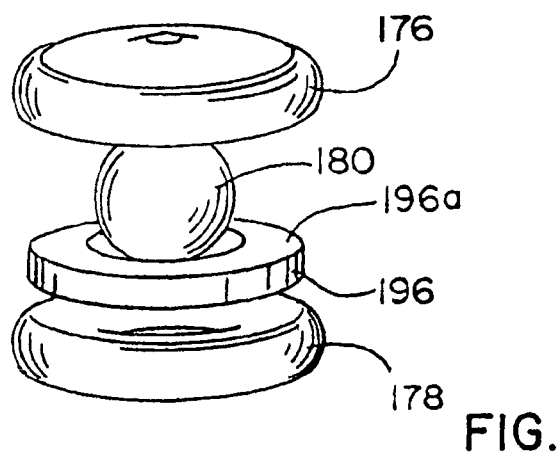
Figure 11G:
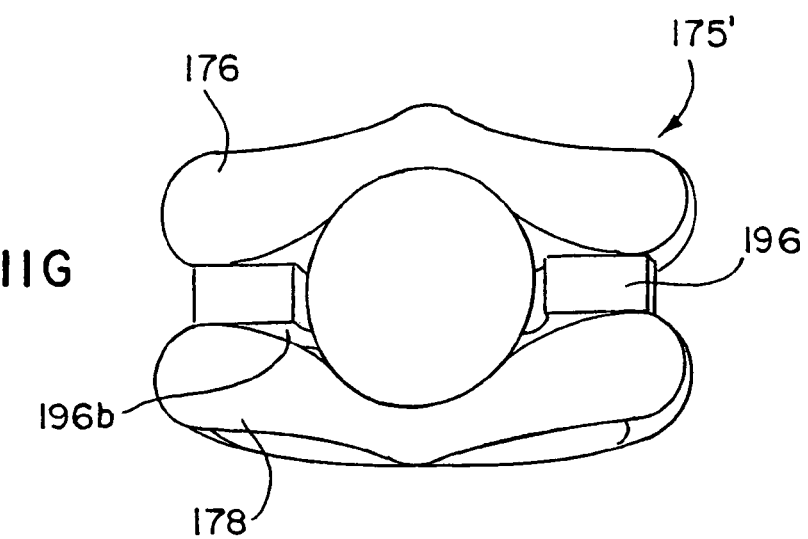
Figure 11H:
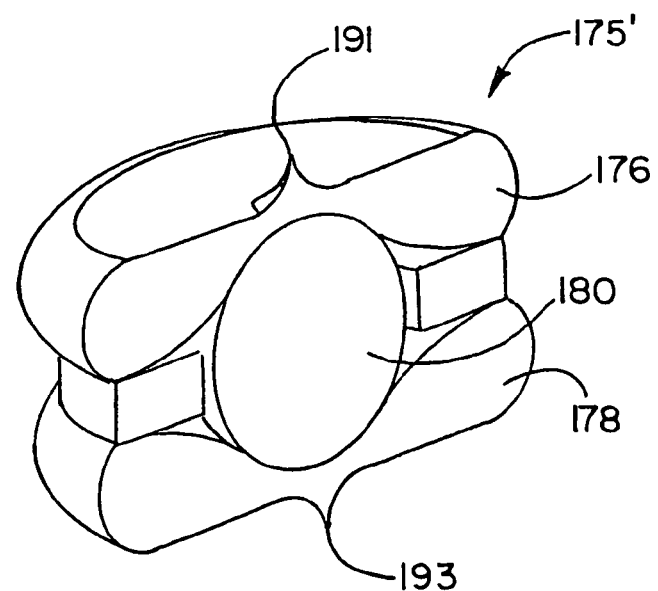

An alternative disc device 175 is shown in FIGS. 11A-11D having upper and lower disc plate members 176 and 178 with there being a load bearing member 180 therebetween. However, unlike prior devices, the device 175 like other devices described herein allows for relative movement between the vertebrae 20 and 22 and the respective vertebral engaging members 176 and 178. The plate members 176 and 178 have arcuate vertebral engaging surfaces 182 and 184 formed thereon having a gradual curvature or slope extending from the outer periphery up toward central axis 186 of the device 175. As the surfaces 182 and 184 approach the axis 186 they begin to extend more axially than radially to form center projections 188 and 190. These projections 188 and 190 are shown in FIGS. 11C and 11D as being provided with a tip or point end 191 and 193 for piercing into the vertebral bone locating the device 175 implanted between the vertebrae 20 and 22 although they also could simply be curved or sloped as shown in FIGS. 11A and 11B to serve the same locating function similar to the center arcuate surface portions of previously-described devices.

Accordingly, the surfaces 182 and 184 include radially extending bearing surface portions 182a and 184a that extend radially along the respective facing vertebral surfaces and central, axially extending bearings surface portions 182b and 184b that serve to locate the device 175 while also allowing relative sliding rotation of the vertebrae 20 and 22 thereabout and specifically 360° about device axis 186 since the plate members 176 and 178 are not fixed to the respective vertebrae 20 and 22. The center surface portion 182b and 184b only resist lateral sliding of the plates 176 and 178 by fitting in correspondingly shaped recesses or openings in the vertebral facing surfaces 20 and 22a and otherwise are not fixed or fastened thereto.

As shown, the member 180 has a spherical ball configuration. The plates 176 and 178 have arcuate recessed surfaces 192 and 194 opposite their surfaces 182 and 184 and in which the ball member 180 seats. The ball member 180 can be of a harder material, e.g. steel, than the softer disc plate members 176 and 178. The materials for the members 176-180 is preferably selected for low frictional resistance to relative sliding movement therebetween to allow rotation of the members 176-180 such as when the spine is twisted and to allow relative sliding between the plate members 176 and 178 and ball 180 such as when the spine is bent in flexion and extension with the plates 176 and 178 pivoting with respect to each other. In this manner, the device 175 is bi-polar since there are two shifting interfaces thereof, i.e. between the plates 176 and 178 and the vertebrae 20 and 22 and between the ball 180 and the plates 176 and 178.

FIGS. 11E-11H are views of another device 175' similarly constructed to device 175 including upper and lower plates 176 and 178 with a ball bearing 180 therebetween. The device 175' also includes an annular member 196 that extends about the ball bearing 180 with the plates 176 and 178 engaged against upper and lower surfaces 196a and 196b thereof. The annular member 196 acts as a shock absorber and can be formed of an elastomeric or other resilient material.

As is apparent, the various forms of artificial disc devices disclosed herein rely on both a center bearing portion and an outer, annular bearing portion extending about the center bearing portion to provide implants that resist migration without relying on disc fixing mechanisms such as intrusive bone fasteners, clamps and the like while also avoiding subsidence problems about the center bearing portion. To this end, the upper and lower arcuate surfaces of the center bearing or bearing portion or bearing assembly seat in correspondingly shaped recesses 27 and 29 in the vertebral surfaces 20a and 22a to locate the artificial disc device between the vertebrae 20 and 22. The interface between the center bearing surface portions and the recesses 27 and 29 is preferably a sliding one, i.e. not fixed, to substantially provide the vertebrae with their normal range of motion relative to each other with the discs implanted therebetween. And because of the enlarged axial spacing of the surface portions relative to the outer bearing portion, be they formed on separate components such as the dome shells or on a single part such as center ball or post bearings, the convex curvature of the center surface portions seated in the concave recesses provides resistance against migration or lateral shifting of the device out from between the vertebrae.

Extending about these axially projecting center bearing surface portions are outer bearing surface portions that also extend radially outwardly therefrom, generally with a more gradual curvature or with a flat configuration. As shown, the outer bearing surface portions extend so that their radial outer ends are close to the periphery of the respective vertebral bodies thereabove and therebelow. Accordingly, the upper outer bearing surface portion is generally lower than the axially projecting upper center bearing surface portion, and they form a juncture at which the direction in which the surface portions of the disc device for engaging the vertebrae changes or transitions from one extending more axially to one extending more radially. This juncture is a direction transition area and does not necessarily mean that the surface portions are joined thereat, such as can be seen with the previously-described ball bearing 12 and ring bearing 14 which are separate components with the ring bearing 14 extending annularly around the ball bearing 12 so as to allow for relative movement therebetween. Similarly, the lower outer bearing surface portion is generally higher than the axially projecting lower center bearing surface portion, and at their juncture the direction of the vertebral engagement surface portion of the device also changes as described above with respect to the upper vertebral engagement surface portions. In this manner, these radially extending outer surface portions limit the ability of the vertebrae or their attached end plates to subside around the center bearing. If there is any subsidence, its extent is limited by the axial spacing of the upper and lower outer bearing surface portions. In other words, in the area taken up by the artificial disc, the spacing of the upper and lower vertebrae can not be less than the spacing between the outer bearing surface portions, thereby limiting subsidence problems accordingly.

In another version of a disc device 200 in accordance with the above principles, upper and lower arcuate center bearing surface portions 202 and 204 that are convexly curved are provided for locating the device 200 between adjacent vertebrae in corresponding arcuate concave recesses formed therein. Upper and lower outer bearing surface portions 206 and 208 extend annularly about respective center bearing surface portions 202 and 204 and limit subsidence between the vertebrae about the center bearing portion 210 of the device 200. The upper surface portions 202 and 206 are formed integrally on an upper plate member 212, and the lower surface portions 204 and 208 are formed integrally on a lower plate member 214. The plate members 212 and 214 can be of a hard biocompatible material such as titanium coated with a pyrolitic carbon. Like previously-described discs, the center bearing surface portions 202 and 204 are spaced by an axially greater distance than the outer bearing surface portions 206 and 208, and they have a smaller radius of curvature than the more gradual curvature of the surface portions 206 and 208. As such, as the vertebral engaging surface portions extend away from the disc axis 216, there is upper and lower junctures 218 and 220 where the direction and configuration of the surface portions undergo an abrupt change from one where the surface portion 202 or 204 extends more axially versus one where the surface portion 206 or 208 extends more radially to provide subsidence resistance about the center bearing 210. To this end, the plate members 212 and 214 include respective small, axial projections 213 and 215 that are centrally disposed relative to disc axis 216 and on which the respective center bearing surface portions 202 and 204 are formed.

As part of annular, outer bearing portion or assembly 222 extending about the center bearing assembly 210, an annular load bearing portion or member 224 is provided axially between the upper and lower bearing plates 212 and 214. The member 224 is preferably of a resilient material such as an elastomeric or resiliently compressible polymeric material, e.g. polyurethane and silicone combination, or a hydrogel material, for taking loads that are generated between the vertebrae during normal spinal movements. The annular member 224 has an axial thickness sized to maintain the plates 212 and 214 spaced axially by an anatomically correct distance from each other for engaging the vertebrae and keeping them properly spaced. At the same time, the resilient material of the load bearing member 224 allows the plates 212 and 214 to shift or deflect relative to each other during dynamic relative movements of the spine vertebrae 20 and 22 such as when the spine is being twisted and bent as in flexion or extension movements. For example, at one end of the disc 200, the plates 212 and 214 may be pivoting toward each other compressing the member 224 therebetween while at a generally diametrically opposite end the plates 212 and 214 will pivot or shift away from each other allowing for expansion of the resilient material of the member 224 in this area between the plates 212 and 214.

The annular bearing member 224 can be a composite to include a harder low friction wear coating on its upper and lower surfaces to allow the facing lower and upper surfaces of the respective upper and lower bearing plates 212 and 214 to minimize wear in this interface area such as when compressional and/or torsional forces are applied therebetween. Alternatively, upper and lower annular washers or wear plates 226 and 228 can be inserted in the interfaces between the upper bearing plate 212 and the load bearing member 224 and the lower bearing plate 214 and the load bearing member 224 to allow the plates 212 and 214 to have a low friction surface in engagement therewith.

The annular configuration of the load bearing member 224 of the outer bearing portion 222 forms an interior central space 230 in which a bumper or plug member 232 is provided as part of the center bearing portion 210 of the device 200. The bumper member 232 fits somewhat loosely in the interior space 230 and is of a harder material having a higher modulus of elasticity than the outer bearing member 224. Thus, the plug member 232 is operable during high impact loading on the vertebrae to keep the annular member 224 from deforming too much and overloading. In normal loading conditions, there is a spacing between the upper plate member 212 and the bumper member 232. The harder plug member 232 allows the annular member 224 to be softer so that its cushioning function between the vertebrae can be maximized. At the same time the material of the member 224 needs to be of sufficient stiffness or resiliency so as to be substantially shape retentive for maintaining stability between the vertebrae over millions of cycles and without experiencing undesirable material creep or plastic deformation due to the heavy loading it will undergo.

Figure 12B:
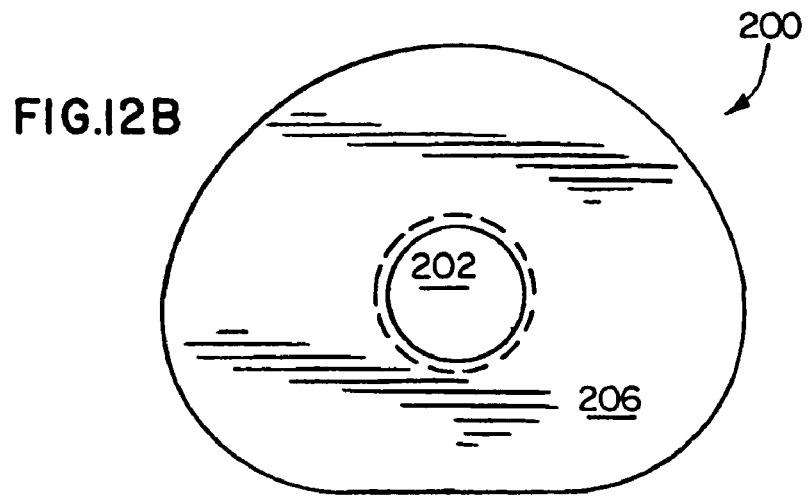
FIGS. 12A-12I are directed to various views of an alternative disc device showing upper and lower plate members, and an annular load bearing member and a plug member therebetween.
Figure 12A:
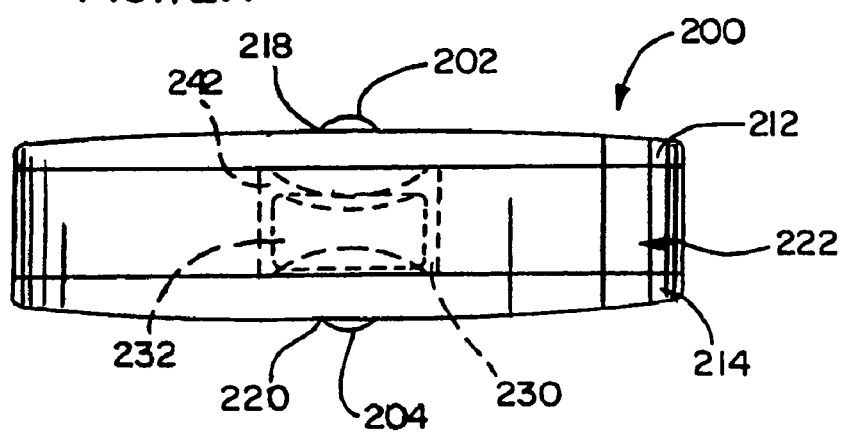
Figure 12C:
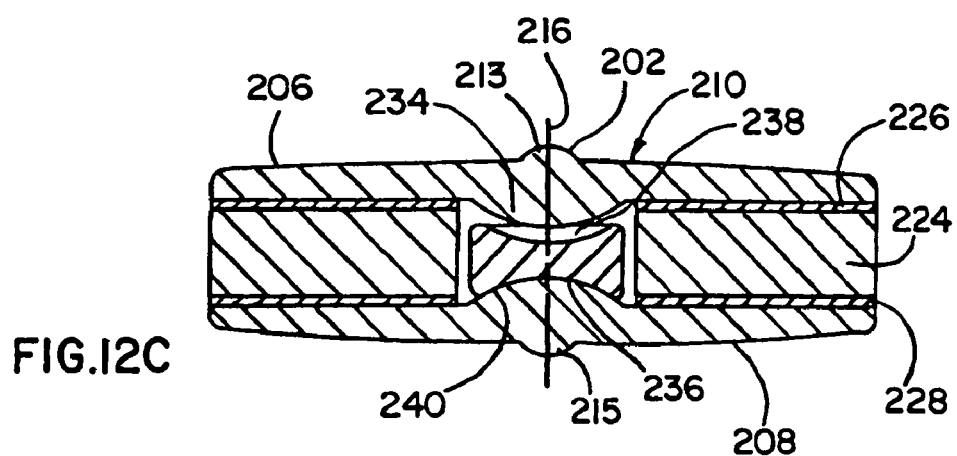

As can be seen in FIGS. 12A and 12C, the plates 212 and 214 have respective arcuate projections 234 and 236 that extend toward each other in the interior space 230. The plug member 232 has upper and lower arcuate recesses 238 and 240 concavely configured to mate with the convex configuration of the arcuate projections 234 and 236, respectively. The relative sizing of the space 230 and the plug member 232 therein is such that when the plug member 232 rests on the lower plate 214 via seating of the projection 236 in the recess 240, there will be an axial gap 242 between the plug 232 and the upper plate 212 and specifically the respective surface 238 and projection 234 thereof. Accordingly, the annular member 224 has a greater axial thickness than the plug member 232. The space 230 has a larger diameter than the plug member 232 so that there is a generally lateral space between the inner surface 224a of the annular member 224 and the plug member 232 allowing for lateral deformation of the resilient member 224 when loaded. When the vertebrae are overloaded such as due to shock or high impact loads, the normal loading ring member 224 is compressed taking up the axial gap 242 such that the projection 234 engages the harder plug member 232 in the recess 238 thereof. In this manner, further compression and overloading of the resilient member 224 is avoided. Also, engagement of the projections 234 and 236 in their recesses 238 and 240 resists relative lateral shifting between the plates 212 and 214, and the annular member 222.

It is also contemplated that the annular member 224 and plug member 232 could be integrally formed with one another, although having the members 224 and 232 as separate components is the preferred form for the present disc device 200.

As best seen in FIG. 12C, the arcuate projections 234 and 236 are larger than the respective arcuate surface portions 202 and 204. The projections 234 and 236 are centrally disposed relative to axis 216 and extend radially for a greater distance on either side of axis 216 than do the arcuate surface portions 202 and 204 so that there is a greater bearing surface interface between the plate projections 234 and 236 and the plug member 232 than between the locating surface portions 202 and 204 and the vertebrae. As such, when the plug member 232 is loaded, it provides relatively large bearing surfaces for the plates 212 and 214, and also allows for pivoting between the plates 212 and 214 with the plate central projections 234 and 236 sliding in respective recesses 238 and 240 and with compression and expansion of generally diametrically opposed portions of the member 224 depending on the exact location of the loads placed on the device 200. Alternatively, the surface portions 202 and 204 can be similarly sized to the projections 234 and 236 or even larger for maximizing the bearing surface area they provide between the device and the vertebrae.

Figure 12D:
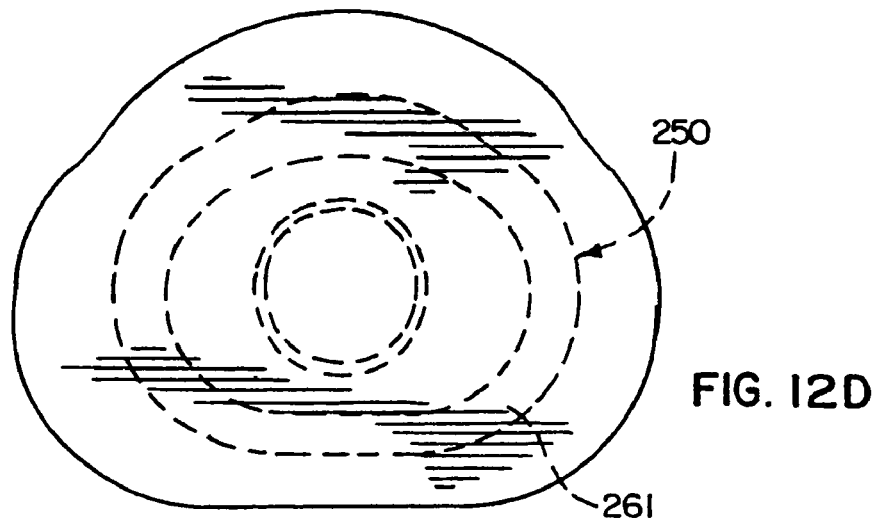
Figure 12E:
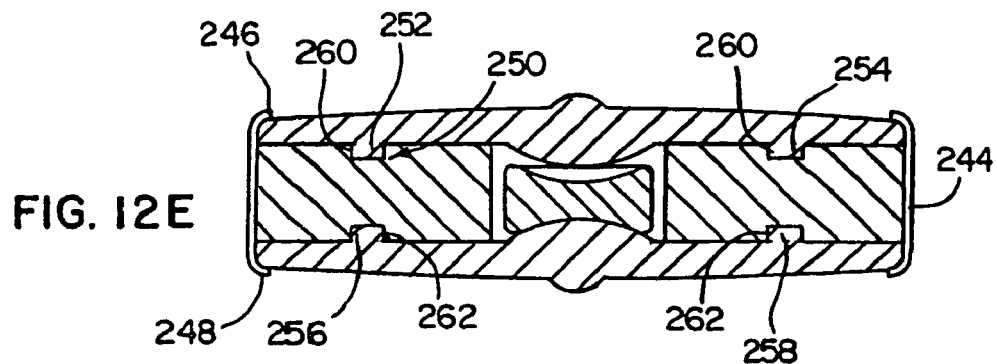

In FIGS. 12D and 12E, the disc device 200 is shown with modifications including an annular sheath 244 that extends about the outer periphery of the device 200. The sheath 244 includes upper and lower lips 246 and 248 and that grip around and onto the upper and lower surfaces 206 and 208, respectively, of the outer bearing assembly 222 to hold the device 200 in its assembled form for implantation. Alternatively, a bag completely encasing the device 200 could be employed. Also, a retaining structure, generally designated 250, can be provided between the plates 212 and 214 and the annular member 224 for resisting relative lateral shifting between the plates 212 and 214, and the member 222, as well as resisting relative rotational shifting therebetween for keeping these disc components aligned. Projecting posts 252 and 254 can project down from the underside of the upper plate 212, and posts 256 and 258 can project up from the upper side of the lower plate 214. Corresponding aperture pairs 260 and 262 can be formed in the upper and lower surfaces of the annular bearing member 224 for receiving the respective post pairs 252, 254 and 256, 258 therein, as can be seen in FIG. 12E. Alternatively, the location of the posts and apertures could be reversed. In another alternative form of retaining structure 250, upper and lower annular grooves 261 (upper groove 261 shown in ghost in FIG. 12D) can be formed in upper and lower surfaces of the annular bearing member 224 for receipt of corresponding upper and lower raised ridges formed on the resilient annular member 224. Since the plan shape or configuration of the plates 212 and 214 and member 224 are other than circular, it is desirable for the ridges and grooves to be similarly configured so that relative rotational sliding as well as translational or lateral sliding between these components is resisted. Again, the components on which the cooperating grooves and ridges are formed can be reversed from that described above.

Figure 12F:
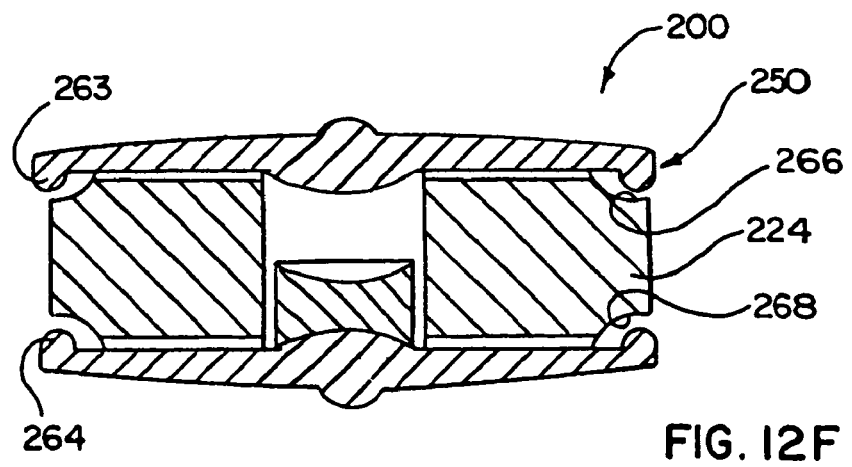

Instead of the posts/recess or groove/ridge structure 250, the structure 250 can be provided at the periphery of the device 200, as shown in FIG. 12F. The upper plate 212 includes a downwardly extending peripheral lip projection 263, and the lower plate 214 includes an upwardly extending peripheral lip projection 264. The resilient member 224 is provided with peripheral grooves 266 and 268 in which the lips 262 and 264 extend so as to restrain the member 224 against lateral and rotational shifting relative to the plates 212 and 214.

Figure 12G:
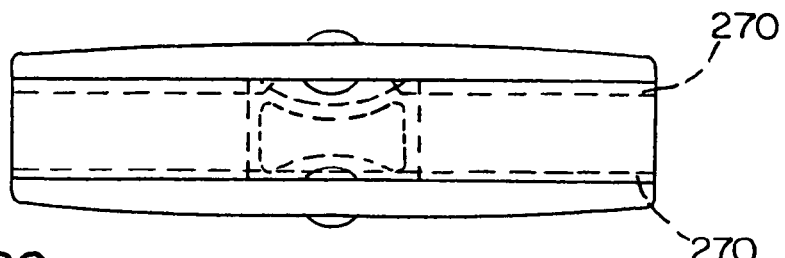
Figure 12H:
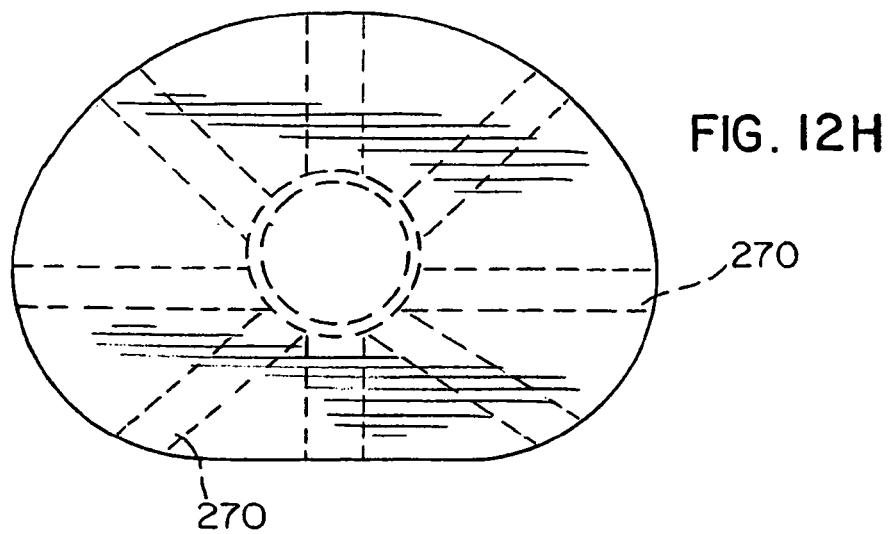
Figure 12I:
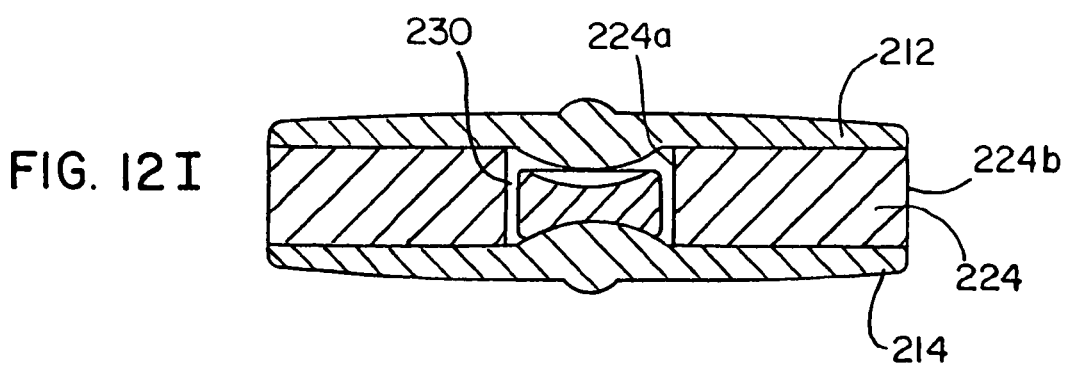

FIGS. 12G-12I show device 200 modified to include upper and lower recessed channels 270 formed in the upper and lower surfaces of the annular member 224 that extend from the inner, axially extending surface 224a to the outer peripheral surface 224b of the member 224 to form openings at each surface. In this way, the interior space 230 in which the plug member 232 is received communicates with the space external to the device 200 via the flowpaths provided by the channels 270. Thus, the channels 270 allow for fluid flow into and out from the device between the plates 212 and 214 and the annular member 224. The channels 270 also keep vacuum conditions from developing in the space 230 as its volume continually varies with vertebral movements and thus the channels 270 serve as a vacuum breaker for the device 200. The channels 270 can be provided in a radial pattern so that there are several pairs of channels 270 extending in radially opposite directions from the center space 230, as best seen in FIG. 12H.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. An artificial disc device for being implanted entirely within an annulus between endplates of the upper and lower vertebrae, the artificial disc device comprising:
   upper and lower bearing members each having integral one-piece bodies sized to fit entirely within the annulus, the one-piece bodies having inner facing surfaces and respective smooth outer bearing surfaces comprising a polymer that are entirely free from bone engaging teeth or surface roughening and generally extending in a radial direction for projecting along and slidingly engaging against respective surfaces of the endplates of the upper and lower vertebrae;
   shifting interfaces between the smooth outer bearing surfaces of the one-piece bodies of the upper and lower bearing members and the respective surfaces of the upper and lower vertebrae;
   a rigid central bearing portion comprising rigid upper and lower inner arcuate surface portions in engagement with one another with at least one of the inner arcuate surface portions being formed integrally on the inner facing surface of one of the one-piece bodies of the upper and lower bearing members for providing a shifting interface therebetween, wherein the inner arcuate surface portions each have a generally spherical contour with a generally constant radius of curvature from a reference center point and being sized for allowing polyaxial movement between the upper and lower bearing members, and the one-piece bodies of the bearing members being configured so that the engaged, spherical arcuate surface portions provide for substantially 360 degree unrestricted twisting rotational movement between the upper and lower bearing members about a centrally disposed vertical axis extending transverse to the radial direction;
   opposite radially outer portions of the one-piece bodies of the bearing members each having a substantially semi-circular outer edge in a plane transverse to the vertical axis and sized and configured to fit within the annulus and that are configured to be shifted for substantially 360 degrees from an aligned position with the opposite radially outer portions of each of the one-piece bodies of the bearing members overlapping each other, to offset positions with the opposite radially outer portions offset from each other, and back to the aligned position via the twisting rotational movement between the bearing members to turn the opposite radially outer portions thereof to rotate about the vertical axis; and
   peripheries extending about each of the one-piece bodies of the bearing members configured so that the one-piece bodies of the bearing members generally have a geometric center thereof with the generally spherical, inner arcuate surface portions arranged so that with the one-piece bodies of the bearing members each extending generally parallel to one another, the geometric centers of the one-piece bodies of the bearing members are aligned, so that the vertical axis extends through the geometric centers of the one-piece bodies of the bearing members and the reference center points of the inner arcuate surface portions.

2. The artificial disc device of claim 1, wherein the upper arcuate surface portion is a concave surface formed on an inner surface of the upper bearing member.

3. The artificial disc of claim 1, wherein the inner facing surfaces include generally radially extending surface portions that generally face each other and extend away from the centrally disposed arcuate surface portions.

4. The artificial disc device of claim 3, wherein the upper and lower inner arcuate surface portions are disposed on centrally located raised portions that protrude inwardly from the generally radially extending surface portions of the inner surfaces.

5. The artificial disc device of claim 3, wherein the radially extending surface portions extend from the centrally disposed upper and lower arcuate surface portions along the opposite portions of the bearing members and are free of bearing surfaces to allow polyaxial movement and substantially 360 degree unrestricted twisting rotational movement between the upper and lower bearing members via the single central bearing portion.

6. The artificial disc device of claim 1, wherein the upper and lower arcuate surface portions comprise a polymer.

7. The artificial disc device of claim 1, wherein the smooth outer bearing surfaces comprise a coating.

8. The artificial disc device of claim 1, wherein the upper and lower inner arcuate surface portions are disposed respectively on inner surfaces of the upper and lower bearing members and are configured for directly engaging with one another without an intermediate bearing member between the inner surfaces.

* * * * *